(12) United States Patent
Cullen et al.

(10) Patent No.: US 9,267,145 B2
(45) Date of Patent: Feb. 23, 2016

(54) METHOD OF REGULATING GENE EXPRESSION

(71) Applicant: DUKE UNIVERSITY, Durham, NC (US)

(72) Inventors: Bryan R. Cullen, Durham, NC (US); Yan Zeng, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 13/737,662

(22) Filed: Jan. 9, 2013

(65) Prior Publication Data

US 2013/0191935 A1 Jul. 25, 2013

Related U.S. Application Data

(63) Continuation of application No. 13/356,514, filed on Jan. 23, 2012, now Pat. No. 8,409,796, which is a continuation of application No. 10/429,249, filed on May 5, 2003, now Pat. No. 8,137,910.

(60) Provisional application No. 60/377,224, filed on May 3, 2002.

(51) Int. Cl.
*C12N 15/82* (2006.01)
*C12N 15/11* (2006.01)
*C07H 21/04* (2006.01)

(52) U.S. Cl.
CPC ............ *C12N 15/8218* (2013.01); *C07H 21/04* (2013.01); *C12N 15/111* (2013.01); *C12N 15/8241* (2013.01); *C12N 2310/111* (2013.01); *C12N 2310/14* (2013.01); *C12N 2310/53* (2013.01); *C12N 2330/30* (2013.01)

(58) Field of Classification Search
USPC ......................................................... 536/24.5
See application file for complete search history.

(56) References Cited

U.S. PATENT DOCUMENTS

| 6,287,844 B1 | 9/2001 | Szafranski et al. |
| 6,429,301 B1 | 8/2002 | Baskerville et al. |
| 6,506,559 B1 | 1/2003 | Fire et al. |
| 7,056,704 B2 | 6/2006 | Tuschl et al. |
| 7,078,196 B2 | 7/2006 | Tuschl et al. |
| 7,232,806 B2 | 6/2007 | Tuschl et al. |
| 7,387,896 B2 | 6/2008 | Turner et al. |
| 2002/0086356 A1 | 7/2002 | Tuschl et al. |
| 2002/0173478 A1 | 11/2002 | Gewirtz |

(Continued)

FOREIGN PATENT DOCUMENTS

| EP | 01042462 | 10/2000 |
| EP | 01123453.1 | 9/2001 |

(Continued)

OTHER PUBLICATIONS

Zeng et al. The EMBO Journal 2005 vol. 24:138-148.*

(Continued)

*Primary Examiner* — Terra Cotta Gibbs
(74) *Attorney, Agent, or Firm* — Andrus Intellectual Property Law, LLP

(57) ABSTRACT

The present invention relates, in general, to gene expression and, in particular, to a method of inhibiting the expression of a target gene and to constructs suitable for use in such a method.

31 Claims, 9 Drawing Sheets

(56) References Cited

U.S. PATENT DOCUMENTS

| | | | |
|---|---|---|---|
| 2003/0051263 | A1 | 3/2003 | Fire et al. |
| 2003/0055020 | A1 | 3/2003 | Fire et al. |
| 2003/0056235 | A1 | 3/2003 | Fire et al. |
| 2003/0059944 | A1 | 3/2003 | Lois-Caballe et al. |
| 2003/0068821 | A1 | 4/2003 | Lois-Caballe et al. |
| 2003/0108923 | A1 | 6/2003 | Tuschl et al. |
| 2004/0053876 | A1 | 3/2004 | Turner et al. |
| 2004/0082771 | A1 | 4/2004 | Kasid et al. |
| 2004/0192629 | A1 | 9/2004 | Xu et al. |
| 2004/0203145 | A1 | 10/2004 | Zamore et al. |
| 2004/0229266 | A1 | 11/2004 | Tuschl et al. |
| 2004/0259247 | A1 | 12/2004 | Tuschl et al. |
| 2004/0259248 | A1 | 12/2004 | Tuschl et al. |
| 2004/0268441 | A1 | 12/2004 | Vance et al. |
| 2005/0026278 | A1 | 2/2005 | Tuschl et al. |
| 2005/0037988 | A1 | 2/2005 | Zamore et al. |
| 2005/0059005 | A1 | 3/2005 | Tuschl et al. |
| 2005/0181382 | A1 | 8/2005 | Zamore et al. |
| 2005/0182005 | A1 | 8/2005 | Tuschl et al. |
| 2005/0186586 | A1 | 8/2005 | Zamore et al. |
| 2005/0214818 | A1 | 9/2005 | Theurkauf et al. |
| 2005/0221293 | A1 | 10/2005 | Tuschl et al. |
| 2005/0221490 | A1 | 10/2005 | Tuschl et al. |
| 2005/0222067 | A1 | 10/2005 | Pfeffer et al. |
| 2005/0227256 | A1 | 10/2005 | Hutvagner et al. |
| 2005/0227934 | A1 | 10/2005 | Stoffel et al. |
| 2005/0234006 | A1 | 10/2005 | Tuschl et al. |
| 2005/0234007 | A1 | 10/2005 | Tuschl et al. |
| 2005/0256072 | A1 | 11/2005 | Aronin et al. |
| 2006/0009402 | A1 | 1/2006 | Zamore et al. |
| 2006/0134787 | A1 | 6/2006 | Zamore et al. |
| 2006/0166910 | A1 | 7/2006 | Tuschl et al. |
| 2006/0212950 | A1 | 9/2006 | Tuschl et al. |

FOREIGN PATENT DOCUMENTS

| | | |
|---|---|---|
| EP | 02006712 | 3/2002 |
| EP | 02016772.2 | 7/2002 |
| EP | 01235842 | 9/2002 |
| WO | WO 99/32619 | 7/1999 |
| WO | WO99/49029 | 9/1999 |
| WO | WO99/53050 | 10/1999 |
| WO | WO 01/29058 | 4/2001 |
| WO | WO 01/42443 | 6/2001 |
| WO | WO 01/75164 | 10/2001 |
| WO | WO01/96584 | 12/2001 |
| WO | WO 02/44321 | 6/2002 |
| WO | WO 02/081628 | 10/2002 |
| WO | WO 03/006477 | 1/2003 |
| WO | WO03/020931 | 3/2003 |
| WO | WO 03/022052 | 3/2003 |
| WO | WO 03/023015 | 3/2003 |
| WO | WO 03/029459 | 4/2003 |
| WO | WO2004/073390 | 9/2004 |

OTHER PUBLICATIONS

Zeng et al. RNA, 2003 vol. 9:112-123.*
Supplementary European Search Report re EP Appln. No. 03747661.
International Search Report re Int'l Patent Appln. No. PCT/US03/13923.
Lagos-Quintana et al, "Identification of Novel Genes Coding for Small Expressed RNAs", Science 294:853-857 (2001).
Lee and Ambros, "An Extensive Class of Small RNAs in Caenorhabditis elegans", Science 294:862-864 (2001).
Lau et al, "An Abundant Class of Tiny RNAs with Probable Regulatory Roles in Caenorhabditis elegans", Science 294:858-861 (2001).
Fire et al, "Potent and specific genetic interference by double-stranded RNA in Caenorhabditis elegans", Nature 39 :806-861 (2001).
Ambros, "microRNAs: Tiny Regulators with Great Potential", Cell 107:823-826 (2001).
Paddison et al, "Short hairpin RNAs (shRNAs) induce sequence-specific silencing in mammalian cells", Genes & Development 16(8):948-958 (2002).
McManus et al, "Gene silencing using micro-RNA designed hairpins", RNA 8(6):842-850 (2002).
Zeng and Cullen, "Sequence requirements for micro RNA processing and function in human cells", RNA 9:112-123.
Coburn and Cullen, "Potent and Specific Inhibition of Human Immunodeficiency Virus Type 1 Replication by RNA Interference", Journal of Virology 76(18):9225-9231 (2002).
Zeng et al, "Both Natural and Designed Micro RNAs Technique Can Inhibit the Expression of Cognate mRNAs When Expressed in Human Cells", Molecular Cell 9:1-20 (2002).
Coburn and Cullen, "siRNAs: a new wave of RNA-based therapeutics", Journal of Antimicrobial Chemotherapy 51:753-756 (2003).
Cullen, Bryan R., "RNAi the natural way", Nature Genetics 37(11): 1163-1165 (2005).
Silva et al, "Second-generation shRNA libraries covering the mouse and human genome", Nature Genetics Advance Online Publication I -:8 (2005)—doi:10.1038/ng1650.
Stegmeier et al, "A lentiviral microRNA-based system for single-copy polymerase II-regulated RNA interference in mammalian cells", PNAS 102(37):13212-13217 (2005).
Dickins et al, "Probing tumor phenotypes using stable and regulated synthetic microRNA precursors", Nature Genetics 37:1289-1296 (2005).
Zeng et al, "Recognition and cleavage of primary microRNA precursors by the nuclear processing enzyme Drosha", The EMBO Journal 24:138-148 (2005).
Cullen, Bryan R., "Is RNA interference involved in intrinsic antiviral immunity in mammals?", Nature Immunology 7(6):563-567 (2006).
Zeng and Cullen, "Efficient Processing of Primary microRNA Hairpin by Drosha Requires Flanking Nonstructured RNA Sequences", The Journal of Biological Chemistry 280(30):27595-27603 (2005).
Cullen, Bryan R., "Derivation and function of small interfering RNAs and microRNAs", Virus Research 102:3-9 (2004).
Zeng et al, "Both Natural and Designed Micro RNAs Technique Can Inhibit the Expression of Cognate mRNAs When Expressed in Human Cells", Molecular Cell 9:1327-1333 (2002).
Zeng et al, "Use of RNA Polymerase II to Transcribe Artificial MicroRNAs", Methods in Enzymology 392 371-380 (2005).
Chen et al, "MicroRNAs Modulate Hematopoietic Lineage Differentiation", Science 303:83-86 (2004).
Lee et al, "The nuclear RNase III Drosha initiates microRNA processing", Nature 425:415-419 (2003).
Chang et al, "Lessons from Nature: microRNA-based shRNA libraries", Nature Methods 3(9):707-14 (2006).
Bartel, David P., "MicroRNAS: Genomics Biogenesis, Mechanism, and Function", Cell 116:281-297 (2004).
Brummelkamp et al, "A System for Stable Expression of Short Interfering RNAs in Mammalian Cells", Science 296:550-553 (2002).
Paul et al, "Effective expression of small interfering RNA in human cells", Nature Biotech, 20:505-508 (2002).
Yu et al, "RNA interference by expression of short-interfering RNAs and hairpin RNAs in mammalian cells", PNAS 99(9):6047-6052 (2002).
Sui et al, "A DNA vector-based RNAi technology to suppress gene expression in mammalian cells", Pnas 99(8):5515-5520 (2002).
Downward, Julian, "RNA interference", BMJ 328:1245-1248 (2004).
Paroo and Corey, "Challenges for RNAi in vivo", TRENDS in Biotechnology 22(8):390-394 (2004).
Fjose and Drivenes, "RNAi and MicroRNAs: From Animal Models to Disease Therapy", Birth Defects Research (Part C) 78:150-171 (2006).
Samarsky et al, "RNAi in drug development: Practical considerations", 27:384-395 (2005), RNA Interference Technology, From Basic Science to Drug Development, Edited by Krishnarao Appasani, Cambridge University Press.
Lu and Woodle, "Delivering siRNA in in vivo for functional genomics and novel therapeutics", 22:303-317 (2005), RNA Interference Technology, From Basic Science to Drug Development, Edited by Krishnarao Appasani Cambridge University Press.

(56) References Cited

OTHER PUBLICATIONS

Zeng et al, "MicroRNAs and small interfering RNAs can inhibit mRNA expression by similar mechanisms", PNAS 100:9779-9784 (2003).
Doench et al, "siRNAs can function as miRNAs", Genes & Development 17:438-442 (2003).
McManus and Sharp, "Gene Silencing in Mammals by Small Interfering RNAs", Nature Reviews, Genetics 3:737-747.
Lee et al, "MicroRNA maturation: stepwise processing and subcellular localization", The EMBO Journal 21(17):4663-4670 (2002).
Hutvágner and Zamore, "A microRNA in a Multiple-Turnover RNAi Enzyme Complex", Science 297:2056-2060 (2002).
Krichevsky et al, "A microRNA array reveals extensive regulation of microRNAs during brain development", RNA 9:1274-1281 (2003).
Hutvágner and Zamore, "RNAi: nature abhors a double-strand", Current Opinions in Genetics & Development 225-232 (2002).
Yi et al, "Exportin-5 Mediates the Nuclear Export of Pre-microRNAs and Short Hairpin RNAs", Genes & Dev. 17:3011-3016 (2013).
Caplen et al, "dsRNA-mediated gene silencing in culture Drosophila cells: a tissue culture model for the analysis of RNA interference", Gene 252:95-105 (2000).
Wianny and Zernicka-Goetz, "Specific interference with gene function by double-stranded RNA in early mouse development", Nature Cell Biology 2:70-75 (2000).
Billy et al, "Specific interference with gene expression induced by long, double-stranded RNA in mouse embryonal teratocarcinoma cell lines", Proc. Natl. Acad. Sci. USA 98(25):14428-14433 (2001).
Elbashir et al, "Duplexes of 21-nucleotide RNAs mediate RNA interference in cultured mammalian cells", Nature 411:494-498 (2001).
Xia et al, "SiRNA-mediated gene silencing in vitro and in vivo", Nature Biotechnology 20:1006-1010 (2002).
Tiscornia et al, "A general method for gene knockdown in mice by using lentiviral vectors expressing small interfering RNA", Proc. Natl. Acad. Sci. USA 100(4):1844-1848 (2003).
Rubinson et al, "A lentivirus-based system to functionally silence genes in primary mammalian cells, stem cells and transgenic mice by RNA interference", Nature Genetics 33:401-406(2003).
Stewart et al, "Lentivirus-delivered stable gene silencing by RNAi in primary cells", RNA 9:493-501 (2003).
Han et al, "Molecular Basis for the Recognition of Primary microRNAs by the Drosha-DGCR8 Complex", Cell 125:887-901 (2006).
Zamore, Phillip D., "Ancient Pathways Programmed by Small RNAs", Science 296:1265-1269 (2002).
Lee et al, "Inhibition of Human Immunodeficiency Virus Type 1 Replication in Primary Macrophages by Using Tat- or CCR5-Specific Small Interfering RNAs Expressed from a Lentiviral Vector", Journal of Virology 77(22):11964-11972 (2003).
Llave et al, "Endogenous and Silencing-Associated Small RNAs in Plants", The Plant Cell 14:1605-1619 (2002).
Reinhart et al, "MicroRNAs in plants", Genes & Development 16:1616-1626 (2002).
Pfeifer et al, "Transduction of Liver Cells by Lentiviral Vectors: Analysis in Living Animals by Fluorescence Imaging", Molecular Therapy 3(3):319-322 (2001).
Aiuti et al, "Correction of ADA-SCID by Stem Cell Gene Therapy Combined with Nonmyeloablative Conditioning", Science 296:2410-2413 (2002).
Kohn et al, "T lymphocytes with a normal ADA gene accumulate after transplantation of transduced autologous umbilical cord blood CD34+ cells in ADA-deficient SCID neonates", Nature Medicine 4(7):775-780 (1998).
Lee et al, "The C. elegans Heterochronic Gene lin-4 Encodes Small RNAs with Antisense Complementarity to lin-14", Cell 75:843-854 (1993).
Onodera et al, "Successful Peripheral T-Lymphocyte-Directed Gene Transfer for a Patient With Severe Combined Immune Deficiency Caused by Adenosine Deaminase Deficiency", Blood 91:30-36 (1998).

Pasquinelli et al, "Conservation of the sequence and temporal expression of let-7 heterochronic regulatory RNA", Nature 408:86-89 (2000).
Dickins et al, "Tissue-specific and reversible RNA interference in transgenic mice", Nature Genetics 39(7):914-921 (2007).
Zhu et al, "A versatile approach to multiple gene RNA interference using microRNA-based short hairpin RNAs", BMC Molecular Biology 8:98 (2007).
Xia et al, "Pol II-Expressed shRNA Knocks Down Sod2 Gene Expression and Causes Phenotypes of the Gene Knockout in Mice", PLoS Genetics 2(1):0073-0080 (2006).
Shin et al, "A single lentiviral vector platform for microRNA-based conditional RNa interference and coordinated transgene expression", PNAS 103(37):13759-13764 (2006).
Definition of "excise", Webster's Third New International Dictionary of the English Language Unabridged, ed. Philip Babcock Gave, Ph.D. and The Meriam-Webster Editorial Staff, Merriam-Webster Inc., Publishers, Springfield, Massachusetts, U.S.A.
McBride et al, "Artificial miRNAs mitigate shRNA-mediated toxicity in the brain: Implications for the therapeutic development of RNAi", PNAS 105(15):5868-5873 (2008).
Paddison et al, "Stable suppression of gene expression by RNAi in mammalian cells", PNAS 99(3):1443-1448 (2002).
Chung et al, "Polycistronic RNA polymerase II expression vectors for RNA interference based on BIC/miR-155", Nucleic Acid Research 34(7):e53 (2006).
Zeng and Cullen, "Efficient Processing of Primary microRNA Hairpins by Drosha Requires Flanking Nonstructured RNA Sequences", The Journal of Biological Chemistry 280(30):27595-27603 (2005).
McLaughlin et al, "Sustained suppression of Bcr-Abl-driven lymphoid leukemia by microRNA mimics", PNAS 104(51):20501-20506 (2007).
Silva et al, "Second-generation shRNA libraries covering the mouse and human genomes", Nature Genetics 37(11):1281-1288 (2005).
U.S. Published Appln. No. 2006/0009402.
Schwab et al, "Highly Specific Gene Silencing by Artificial MicroRNAs in Arabidopsis", The Plant Cell 18:1121-1133 (2006).
Abreu Parizotto et al, "In vivo investigation of the transcription, processing, endonucleolytic activity, and functional relevance of the spatial distribution of a plant miRNA", Genes & Dev, 18:2237-2242 (2004).
Alvarez et al, "Endogenous and Synthetic MicroRNAs Stimulate Simultaneous, Efficient, and Localized Regulation of Multiple Targets in Diverse Species", The Plant Cell 18:1134-1151 (2006).
Qu et al, "Artificial microRNA-mediated virus resistance in plants", J. Virol. 81(12):6690-6696 (2007)—Abstract.
Underwood, "MicroRNAs Flex Their Muscles", ACS Chemical Biology 2(2):86-87 (2007).
Ruvkun, G., "Glimpses of a Tiny RNA World", Science 294:797-799 (2001).
Examiner's Answer dated Apr. 6, 2010 issued in connection with U.S. Appl. No. 10/623,930, filed Jul. 21, 2003.
Board Decision dated Sep. 1, 2011 issued in connection with U.S. Appl. No. 10/623,930, filed Jul. 21, 2003.
Paddison et al, "Short hairpin RNAs (shRNAs) induce sequence-specific silencing in mammalian cells", Genes Dev, 16:948-958 (2002).
Ketting et al, Dicer functions in RNA interference and in synthesis of small RNA involved in developmental timing in C. elegans, Genes Dev, 15:2654-2659 (2001).
McJunkin et al, "Reversible suppression of an essential gene in adult mice using transgenic RNA interference", Proc. Natl. Acad. Sci. USA 108(17):7113-7118 (Epub 2011).
Premsrirut et al, "A Rapid and Scalable System for Studying Gene Function in Mice Using Conditional RNA Interference", Cell 145:145-158 (2011).
Grishok et al, "Genes and Mechanisms Related to RNA Interference Regulate Expression of the Small Temporal RNAs that Control C. elegans Developmental Timing", Cell 106:23-34 (2001).
Reinhart et al, "The 21-nucleotide let-7 RNA regulates developmental timing in Caenorhabditis elegans", Nature 403:901-906 (2000).
Office Action dated Jun. 2, 2009 issued in connection with U.S. Appl. No. 10/623,930 (Pub. No. 20040268441).

(56) References Cited

OTHER PUBLICATIONS

Amendment and Request for Continued Examination filed in connection with U.S. Appl. No. 10/623,930 (Pub. No. 20040268441) on Mar. 4, 2009.
Davis and Hata, "Regulation of MicroRNA Biogenesis: A myriad of mechanisms", Cell Communication and Signaling, 7:18 (2009).
Chung et al, "Polycistronic RNA polymerase II expression vectors for RNA interference based on BIC/miR-155", Nucleic Acids Research 34(7):e53 (2006).
Dickins et al, "Probing tumor phenotypes using stable and regulated synthetic microRNA precursors", Nature Genetics 37(11):1289-1295 (2005).
Niu et al, "Expression of artificial microRNAs in transgenic *Arabidopsis thaliana* confers virus resistance", Nature Biotechnology 24(11):1420-1428 (2006).
Ossowski et al, "Gene silencing in plants using artificial microRNAs and other small RNAs", The Plant Journal 53:674-690 (2008).
Rao et al, "Tissue-specific RNAi reveals that WT1 expression in nurse cells controls germ cell survival and spermatogenesis", Genes Dev. 20:147-152 (2006).
Hannon et al, "Unlocking the potential of the human genome with RNA interference", Nature 431:371-378 (2004).
Murfett et al, "Antisense suppression of S-RNase expression in *Nicotiana* using RNA polymerase II- and III—transcribed gene constructs", Plant Molecular Biology 29:201-212 (1995).
Lottmann et al, "The Tet-On system in transgenic mice: inhibition of the mouse pdx-1 gene activity by antisense RNA expression in pancreatic beta cells", Journal of Mol. Med. 79:321-328 (2001).
Mautino et al, "Inhibition of HIV-1 replication by novel entiviral vectors expressing transdominant Rev and HIV-1 env antisense", Gene Therapy 9:421-431 (2002).
Nathwani et al, "Current status and prospects for gene therapy", Vox Sanguinis 87:73-81 (2004).
Eck and Wilson, Gene-Based Therapy:, Goodman & Gilman's the Pharmacological Basis of Therapies, 9$^{th}$ Edition, Chapter 5, McGraw-Hill, NY.
Verma and Somia, "Gene therapy—promises, problems and prospecs", Nature 389:239-242 (1997).
EPO Communication of a Notice of Opposition, Notice of Opposition and Statement of Grounds of Opposition (in German), mailed Dec. 2, 2014 in EP Application No. 03747661.1, Applicant: Duke University.
Certified English Translation of Statement of Grounds of Opposition mailed Dec. 2, 2014 (dated Nov. 24, 2014) in EP Application No. 03747661.1, Applicant: Duke University (prepared by Janet Hope).
Wesley et al, "Construct design for efficient, effective and high-throughput gene silencing in plants" The Plant Journal (2001) 27(6), 581-590.
Smith et al, "Total silencing by intron-spliced hairpin RNAs" Nature, vol. 407, Sep. 21, 2000, pp. 319-320.
Moss, "MicroRNAs: Hidden in the Genome" Current Biology, vol. 12, R138-R140, Feb. 19, 2002.
Hutvagner et al, "A Cellular Function for the RNA-Interference Enzyme Dicer in the Maturation of the let-7 Small Temporal RNA" Science, vol. 293, Aug. 3, 2001, pp. 834-838.
Bernstein et al., "Role for a bidentate ribonticlease in the initiation step of RNA interference", Nature 409:363-.366 (2001).
Knight and Bass, "A role for the Rnase III enzyme DCR-I in RNA interference and germ line development in Caenorhabditis elegans" Science 293(5538): 2269-2271 (2001).
Nicholson and Nicholson, "Molecular characterization of a mouse cDNA encoding Dicer, a ribonuclease III ortholog involved in RNA interference" Mammalian Genome 13: 67-73 (2002).
Office Action dated Aug. 29, 2006 in U.S. Appl. No. 10/429,249.
Office action dated Apr. 4, 2007 in U.S. Appl. No. 10/429,249.
Office action dated Sep. 18, 2007 in U.S. Appl. No. 10/429,249.
Office action dated Apr. 25, 2008 in U.S. Appl. No. 10/429,249.
Office action dated Dec. 24, 2008 in U.S. Appl. No. 10/429,249.
Office action dated Jul. 22, 2009 in U.S. Appl. No. 10/429,249.
Office action dated Apr. 14, 2010 in U.S. Appl. No. 10/429,249.
Office action dated Sep. 27, 2012 in U.S. Appl. No. 13/356,514.
US 6,124,129, 09/2000, Szafranski et al. (withdrawn)

\* cited by examiner

*Fig. 1A*     mir-30 precursor:
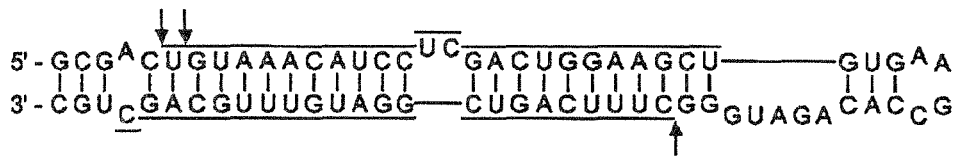
*Fig. 1B*
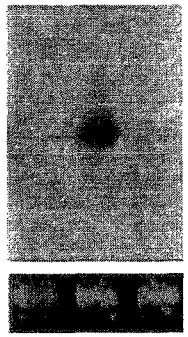
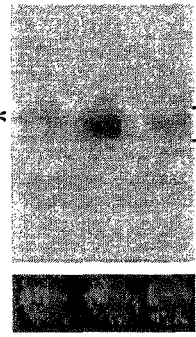
*Fig. 2A*
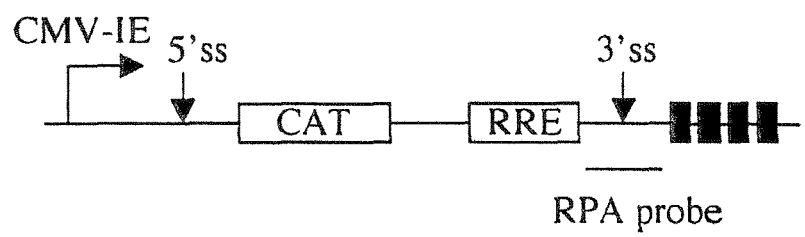

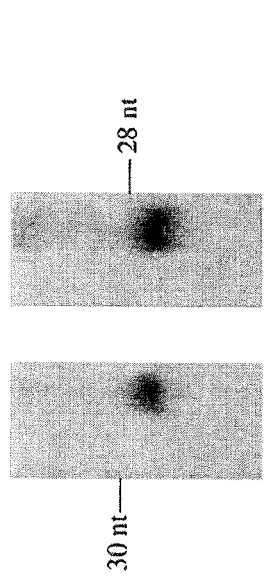
*Fig. 3A* mir-30-nxt precursor:
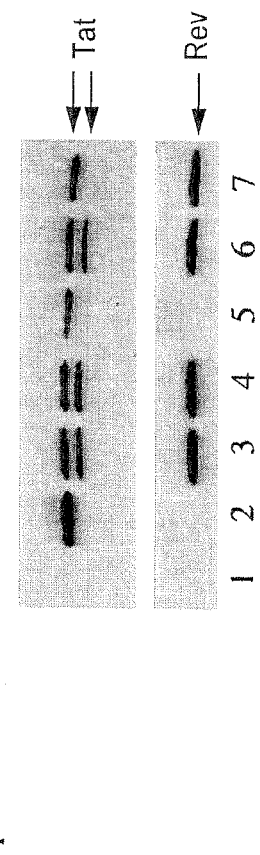
*Fig. 3B*
*Fig. 3C*
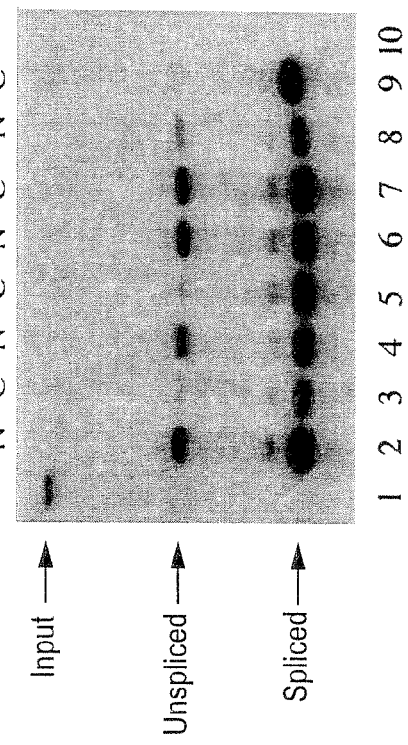
*Fig. 3D*

Mir-30-PTB miRNAs inhibits endogenous PTB expression

Inhibition of Endogenous SV40 T antigen (TAg)
Expression in 293T cells by Mir-30-TAg

Fig. 5A miR-30 miRNA
5'-CUUUCAGUCGGAUGUUUGCAGC-3'
3'-GAAAGUCAG    ACAAACGUCG-5'
            GGA
Target: miR-30(B)

miR-30 miRNA
5'-CUUUCAGUCGGAUGUUUGCAGC-3'
3'-GAAAGUCAGCCUACAAACGUCG-5'
Target: miR-30(P)

anti-miR-30 miRNA
5'-UGUAAACAUCCUCGACUGGAAGCU-3'
3'-CAUUUGUAG    CUGACCUUCG-5'
            CUC
Target: miR-30(AB)

anti-miR-30 miRNA
5'-UGUAAACAUCCUCGACUGGAAGCU-3'
3'-CAUUUGUAGGAGCUGACCUUCG-5'
Target: miR-30(AP)

miR-21 miRNA
5'-UAGCUUAUCAGACUGAUGUUGA-3'
3'-AUCGAAUAG    GACUACAACU-5'
            AGA
Target: miR-21(B)

miR-21 miRNA
5'-UAGCUUAUCAGACUGAUGUUGA-3'
3'-AUCGAAUAGUCUGACUACAACU-5'
Target: miR-21(P)

dNxt siRNA
5'-AUUCCAGCUAAGCGUAGCAUU-3'
3'-UAAGGUCGA    GCAUCGUAA-5'
           AAG
Target: dNxt(B)

dNxt siRNA
5'-AUUCCAGCUAAGCGUAGCAUU-3'
3'-UAAGGUCGAUUCGCAUCGUAA-5'
Target: dNxt(P)

5'-CGGUACAAACCUGCCAGUAAGA-3'
Target: random

Fig. 5B

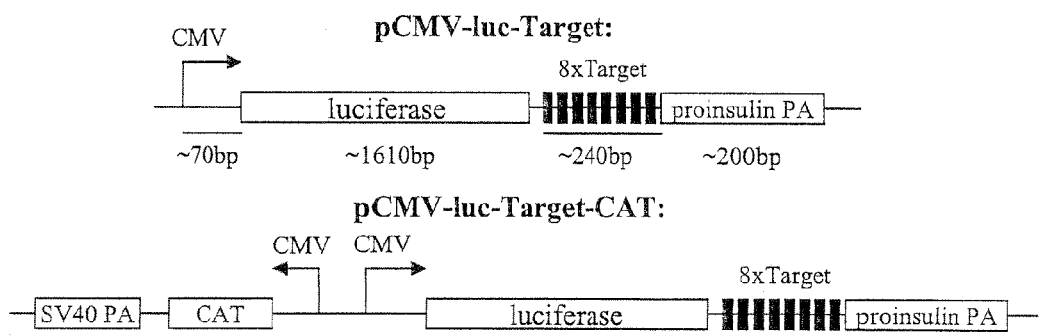

METHOD OF REGULATING GENE EXPRESSION

This application is a continuation of U.S. application Ser. No. 13/356,514, filed Jan. 23, 2012 (now U.S. Pat. No. 8,409, 796 issued Apr. 2, 2013), which is a continuation of U.S. application Ser. No. 10/429,249, filed May. 5, 2003, now U.S. Pat. No. 8,137,910 issued Mar. 20, 2012), which claims priority from Provisional Application No. 60/377,224, filed May. 3, 2002, the entire contents of which are hereby incorporated by reference.

TECHNICAL FIELD

The present invention relates, in general, to gene expression and, in particular, to a method of inhibiting the expression of a target gene, to constructs suitable for use in such a method and to plants and non-human animals comprising such constructs. The invention also relates to compositions and kits comprising constructs that can be used to inhibit gene expression.

BACKGROUND

Animal cells have recently been shown to express a novel class of single-stranded, ~22 nucleotide (nt) non-coding RNAs, termed micro RNAs (miRNAs) (Lagos-Quintana et al, Science 294:853-858 (2001); Lau et al, Science 294:858-862 (2001); Lee and Ambros, Science 294:862-864 (2001)). miRNAs appear to be derived from ~70 nt precursors that form a predicted RNA stem-loop structure. It remains unclear whether these miRNA precursor molecules are transcribed from autonomous promoters or are instead contained within longer RNAs (Ambros, Cell 107:823-826 (2001); Lau et al, Science 294:858-862 (2001)).

While over 100 distinct miRNAs are expressed in organisms as diverse as nematodes (Lau et al, Science 294:858-862 (2001), Lee et al, Science 294:862-864 (2001)), fruit flies (Lagos-Quintana et al, Science 294 858-858 (2002), and humans (Mourelatos et al, Genes Dev. 16:720-728 (2002)), as well as in plants (Tang et al, Genes Dev. 17:49-63 (2003), Reinhart et al, Genes Dev. 16:1616-1626 (2002)), their function remains largely uncertain. However, the biological activity of two miRNAs, *C. elegans* let-7 and lin-4, is well established (Lee et al, Cell 75:843-854 (1993); Reinhart et al, Nature 403:901-906 (2000)). Both lin-4 and let-7 are expressed during specific larval stages and both miRNAs interact with partially complementary RNA targets, located in the 3' untranslated region (3' UTR) of specific mRNAs, to selectively block their translation. This inhibition is important for appropriate developmental regulation in *C. elegans* (Wightman et al, Cell 75:855-862 (1993); Slack et al, Mol. Cell 5:659-669 (2000)).

Several miRNAs, including let-7, are evolutionarily conserved from *C. elegans* to man, as are several let-7 targets (Ambros, Cell 107:823-826 (2001)). This conservation implies that let-7, as well as other miRNAs, may also repress the expression of specific mRNA species in mammalian cells. This hypothesis is also suggested by the similarity between miRNAs and small interfering RNAs (siRNAs), ~21 nt double-stranded RNAs that can induce the degradation of mRNA molecules containing perfectly matched complementary targets, a process termed RNA interference (RNAi) (reviewed by Sharp, Genes Dev. 15:485-490 (2001), see also Hutv<gner et al, Curr. Opin, Genet. Dev. 12:225-232 (2002) and Zamore et al, Science 296:1265-1269 (2002), further see U.S. Pat. No. 6,506,559). However, while miRNAs are encoded within the host genome, siRNAs are generally excised from larger dsRNA precursors produced during viral infection or introduced artificially.

Because the introduction of artificial siRNAs into animal cells can induce the degradation of homologous mRNA molecules, RNAi has emerged as a useful experimental tool (Elbashir et al, Nature 411:494-498 (2001); Fire et al, Nature 391:806-811 (1998); Hammond et al, Nature 404:293-295 (2000)). However, in mammalian cells, induction of RNAi required the transfection of RNA oligonucleotides, which can be inefficient and gives rise to only a transient inhibition in target gene expression.

The present invention provides RNA molecules (miRNAs) functionally equivalent to siRNAs that can be transcribed endogenously in animal and plant cells. The invention makes possible the production of miRNAs specifically designed to inhibit the expression of mRNA containing a complementary target sequence. The miRNA molecules of the invention can be used experimentally or therapeutically to inhibit gene function.

SUMMARY OF THE INVENTION

The present invention relates to artificial miRNAs and to a method of using same to specifically inhibit the expression of selected genes in human and non-human animal cells and in plant cells. In accordance with the invention, an miRNA-encoding DNA sequence is introduced into the cells and inhibition of the target gene is induced by endogenously transcribed miRNAs. Where advantageous, transcription of the miRNA can be placed under the control of an inducible promoter or a tissue specific promoter. As the present method can result in continuous miRNA production, stable inhibition of target mRNA expression can be effected.

Objects and advantages of the present invention will be clear from the description that follows.

BRIEF DESCRIPTION OF THE DRAWINGS

FIGS. 1A-1B. Production of the miR-30 miRNA in transfected cells. (FIG. 1A) (SEQ ID NO:5) Diagram of the predicted human miR-30 precursor RNA (Lagos-Quintana et al, Science 294:853-858 (2001)). Mature miR-30 (3' arm) and anti-miR-30 (5' arm) are indicated lines. Arrows point to the 5' ends of the mature miRNA as determined by primer extension analysis. The position of the 3' ends may have an error of 1 nucleotide. (FIG. 1B) Northern blot analysis of miR-30 and anti-miR-30 in transfected 293T cells. Lanes 1 and 4: RNA from mock-transfected 293T cells. Lanes 2 and 5: cells transfected with pCMV-miR-30. Lanes 3 and 6: cells transfected with pCMV-mmiR-30 (mmiR=mature miR). The relative mobility of synthetic DNA oligos is indicated. "*" indicates the position of a suspected endogenous anti-miR-30 species.

FIGS. 2A-2C. The miR-30 miRNA selectively inhibits expression of an indicator mRNA containing miR-30 target sites. (FIG. 2A) (SEQ ID NOs:6 and 7) The sequence of a designed target site partially complementary to miR-30. pDM128/RRE/4XT was derived from pDM128/RRE by insertion of four copies of this target site into the 3' UTR (black boxes). Splice sites (ss), the RRE and the relative position of the RPA probe are indicated. (FIG. 2B) 293T cells were co-transfected, with 10 ng of an internal control plasmid (pBC12/CMV/β-gal) expressing β-galactosidase (β-gal) and, as indicated, 10 ng of pDMI28/RRE or pDM128/RRE/4XT, 10 ng pcRev, and 400 ng of pCMV-mmiR-30 or pCMV-miR-30. The parental pBC12/CMV plasmid served as the negative control. CAT activities were determined at 48 hrs postransfection and were normalized for β-gal activities. Columns 2 and 6 are arbitrarily set at 100%. (FIG. 2C) 293T cells were transfected with the pDM128/RRE/4XT plasmid, with or without pcRev or pCMV-miR-30, as described in FIG. 2B. At 48 hr. after transfection, cells were divided into nuclear (N) and cytoplasmic (C) fractions, total RNA isolated and analyzed by RPA. The probe fragments rescued by the spliced (S) and unspliced (U) mRNAs encoded by pDM128/RRE/4XT are indicated.

FIGS. 3A-3D. The novel miR-30-nxt miRNA specifically inhibits the cytoplasmic expression of unspliced pgTAT-nxt mRNA. (FIG. 3A) (SEQ ID NO:8) Design of the precursor of the miR-30-nxt miRNA. Inserted sequences derived from the global Drosophila nxt gene are indicated. (FIG. 3B) Detection of the novel miR-30-nxt and anti-miR-30-nxt miRNAs in transfected 293T cells by Northern analysis, Lanes 1 and 3: mock-transfected cells; lanes 2 and 4: pCMV-miR-30-nxt transfected cells. The relative mobility of DNA markers is indicated. (FIG. 3C) Western blots using rabbit polyclonal antisera directed against HIV-1 Tat or Rev. 293T cells were transfected using 25 ng of pgTAT or pgTAT-nxt, 25 ng of pcRev, and 400 ng of pCMV-miR-30-nxt. The parental pBC12/CMV plasmid served as negative control. This Western analysis was performed ~48 hrs. after transfection. (FIG. 3D) The miR-30-nxt miRNA reduces the cytoplasmic level of unspliced pgTAT-nxt mRNA. 293T cells were transfected with pgTAT-nxt, with or without pcRev or pCMV-miR-30-nxt. Two days after transfection, nuclear (N) and cytoplasmic (C) RNAs were prepared and analyzed by RPA, Lane 1 represents approximately 3% of input (I) probe. Probe fragments rescued by spliced (S) and unspliced (U) mRNA are indicated.

(FIG. 4A) Detection of miR-30-PTB and anti-miR-30-PTB expression. 293T cells were mock transfected (lanes 1 and 3) or transfected with pCMV-miR-30-PTB (lanes 2 and 4). After 2 days, total RNA was isolated and used for primer extension analysis. Positions of DNA markers are indicated. (FIG. 4B) Reduction of endogenous PTB protein and mRNA expression by pCMV-miR-30-PTB. Cells were transfected with pCMV-miR-30-nxt (lanes 1 and 3) or pCMV-miR-30-PTB (lanes 2 and 4). After five days, total cell lysates and RNAs were prepared. Lanes 1 and 2: Western blot using antibodies directed against PTB or CA150, which served as a loading control. Lanes 3 and 4: Northern analysis for PTB mRNA. (FIG. 4C) Loss of SV40 Tag in cells transfected with pCMV-miR-30-Tag. Cells were co-transfected with phrGFP-C (a green fluorescent protein expression plasmid) and pCMV-miR-30-nxt or pCMV-miR-30-Tag, and three days later, analyzed by immunofluorescence. (FIG. 4D) Quantitation of cells expressing SV40 Tag, Cells with clear nuclear Tag staining were counted as positive (cytoplasmic staining was weak and also present in secondary antibody-only controls). At least 200 cells were counted for each sample.

FIGS. 5A (SEQ ID NOs:9-25, respectively) and 5B. Indicator construct design. (FIG. 5A) Sequences of the synthetic RNA targets used and their predicted pairing with the miR-30, anti-miR-30 or miR21 miRINA or the dNxt siRNA. Target sequences were either perfectly (P) complementary or were designed to form a central 3 nt bulge (B). A random sequence, for which no complementary small RNA is known to exist, was used as a control. (FIG. 5B) Structure of the pCMV-luc-Target and pCMV-luc-Target-CAT indicator constructs. The Targets, represented by black boxes, are eight tandem repeats of one of the sequences shown in FIG. 5A. PA, polyadenylation signal.

(FIG. 6A) The level of expression of miR-30, anti-miR-30 and of miR-21 in mock transfected 293T cells, or in 293T cells transfected with the indicated miRNA expression plasmids, was determined by primer extension (Zeng et al, RNA 9:112-123 (2003)). (FIG. 6B) The luc enzyme activities detected in 293T cell cultures transfected with the listed indicator and effector plasmids, as well as the pBC12/CMV/β-gal control plasmid, were determined ~40 hr after transfection and then adjusted based on minor variations observed in the CAT internal control. These values are presented normalized to the culture transfected with pCMV-luc-random-CAT and pCMV-miR-21, which was arbitrarily set at 1.0. Average of three independent experiments with standard deviation indicated. The number of nanograms of each miRNA expression plasmid transfected into each culture is indicated. (FIG. 6C) Parallel northern analysis to detect the luc reporter miRNA (top panel) and the control β-gal mRNA (bottom panel), Shown above the top panel are the amounts of pCMV-miR-30 or pCMV-miR-21 transfected per culture. The level of luc enzyme activity detected for each indicator construct is given as a percentage of the level obtained upon co-transfection with the pCMV-miR-21 control plasmid. Lane 1: RNA from mock transfected 293T cells. The arrow indicates the position of the 1.8 kb luc mRNA cleavage product.

(FIG. 7A) This experiment was performed as described in FIG. 6B. Data shown are the average of 4 independent experiments. (FIG. 7B) Parallel northern analysis of luc (upper panel) and β-gal (lower panel) mRNA expression. The level of luc enzyme activity detected with each indicator construct is given as a percentage of the level obtained upon co-transfection with the pCMV-miR-30 control plasmid. Lane 1, RNA from mock transfected 293T cells. The arrow indicates the position of the ~1.8 kb luc mRNA cleavage product.

(FIG. 8A) Cultures were cotransfected with one of the three listed indicator plasmids together with the dNxt or dTap siRNA and the pRL-CMV and pBC12/CMV/β-gal internal control plasmids. The amount of each siRNA used is given in picomoles. Approximately 40 hr after transfection, cultures were used for the dual luciferase assay or for RNA isolation. Firefly luc activities were adjusted for minor variations in the Renilla luc internal control and are presented normalized to the activity observed in the culture transfected with the pCMV-luc-random control plasmid and the dTap control siRNA, which was set at 1.0. These data represent the average of three independent experiments, with standard deviation indicated. (FIG. 8B) Northern analysis of firefly luc (upper panel) and β-gal (lower panel) mRNA expression. The level of firefly luc enzyme activity detected for each indicator construct is given as a percentage of the level obtained with the dTap control siRNA. Lane 1, RNA from a mock transfected culture. The arrow indicates the position of the ~1.8 kb luc mRNA cleavage product.

DETAILED DESCRIPTION OF THE INVENTION

Figure 2B:
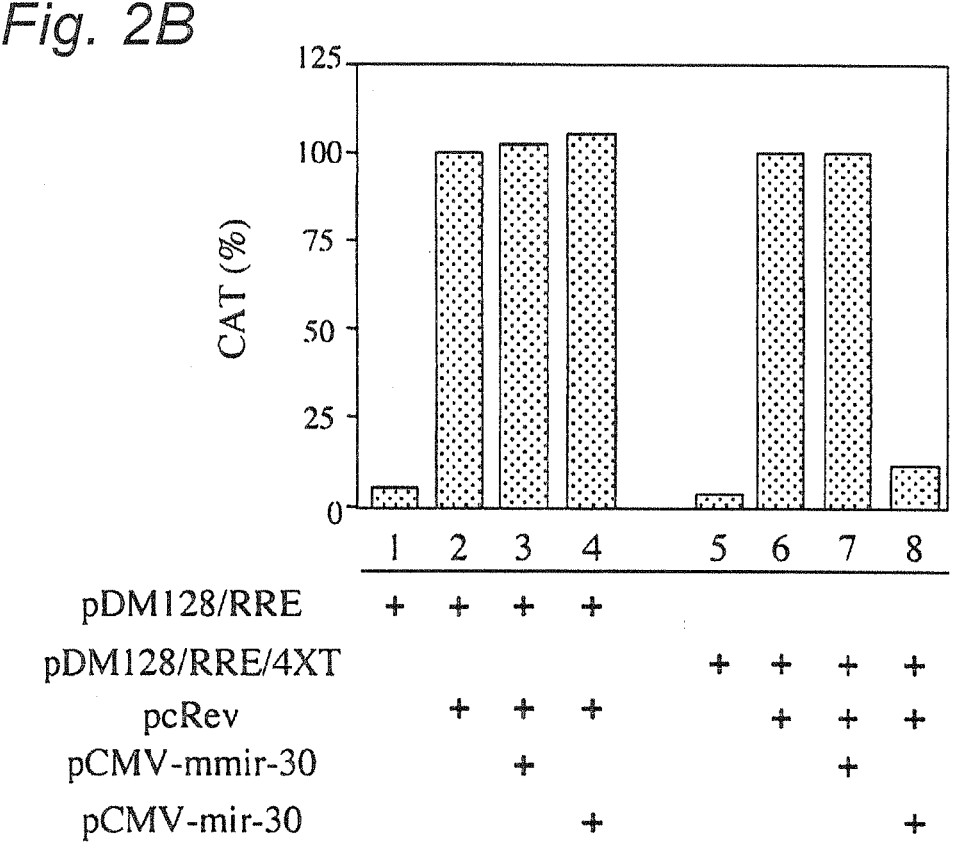

The present invention relates to a method of specifically inhibiting the expression of selected target genes in human and non-human animal cells and in plant cells using endogenously produced miRNA. In accordance with this method, constructs are used that encode one or multiple miRNAs. The constructs are designed such that nuclear processing, transport and excision of mature miRNA are effected efficiently.

The resulting miRNA induces degradation of an mRNA produced in the cell that contains a complementary target sequence or otherwise inhibits translation of the mRNA. The invention further relates to constructs suitable for use in such a method and to compositions and kits comprising such constructs.

In accordance with the present method, a DNA construct is introduced into cells (host cells) in which a target gene sequence is expressed. The construct comprises a promoter functional in the host cells operably linked to a sequence encoding a precursor of the miRNA. Introduction of the construct into the host cells is effected under conditions such that the miRNA precursor transcript is produced and mature miRNA is then excised from the precursor by an endogenous ribonuclease. The resulting mature miRNA induces degradation of the mRNA transcript of the target gene sequence produced in the cell or otherwise inhibits translation of the mRNA. (It will be appreciated that degradation of other types of RNA, including viral RNA, can be similarly induced.)

miRNAs suitable for use in the present invention are, advantageously, about 19-24 nucleotides long, preferably, about 21 or 22 nucleotides in length. The miRNAs can be designed so as to hybridize to any RNA transcript with a high degree of specificity. Advantageously, the miRNA is designed so as to be perfectly complementary to the target sequence within the RNA (e.g., mRNA) as even a single nucleotide reduction in complementarity to the target can, depending on its location, attenuate the level of inhibition. The data presented in Example 2 indicate that miRNA can cleave mRNA bearing a fully complementary target site while miRNA can inhibit expression of mRNA bearing partially complementary sequence without necessarily inducing cleavage. The miRNA can be designed so as to target a 3' or 5' untranslated region of the mRNA or coding region of the mRNA.

As indicated above, the miRNA is excised from a precursor that includes a predicted RNA stem-loop structure (Lagos-Quintana et al, Science 294:853 (2001), Lau et al, Science 294:858 (2001), Lee and Ambrose, Science 294:362 (2001)). This structure stem-loop can be designed such that it is recognized by a ribonuclease (e.g., an RNAse III-type enzyme, such as DICER, or an enzyme having the recognition properties thereof), with the resulting excision of the mature miRNA. Such precursor stem-loop structures can be about 40 to 100 nucleotides long, preferably, about 50 to 75 nucleotides. The stem region can be about 19-45 nucleotides in length (or more), preferably, about 20-30 nucleotides. The stem can comprise a perfectly complementary duplex (but for any 3' tail), however, "bulges" can be present on either arm of the stem and may be preferred. Advantageously, any such "bulges" are few in number (e.g., 1, 2 or 3) and are about 3 nucleotides or less in size. The terminal loop portion can comprise about 4 or more nucleotides (preferably, not more than 25); the loop is preferably 6-15 nucleotides in size. The precursor stem loop structure can be produced as part of a larger, carrier transcript from which the miRNA is excised, or it can be produced as a precise transcript.

The data presented in Zeng et al, RNA 9:112-123 (2003), make clear certain sequence requirements for efficient miRNA processing and functioning (for example, maintenance of base-pairing at the base of the predicted stem, outside the stem portion encoding mature miRNA, being significant), those requirements being incorporated herein by reference. The data presented also demonstrate the desirablity of substituting stem sequences of naturally occurring miRNAs (e.g., miR-30) to generate miRNAs suitable for use in inhibiting expression of any target gene. The data indicate that while the presence of a miR-30 loop may be desirable, variations of that structure can also be tolerated (e.g., loops can be used that are greater than 72%, preferably greater than 79%, more preferably greater than 86%, and most preferably, greater than 93% identical to, for instance, the miR-30 sequence (determined conventionally using known computer programs such as the BESTFIT program (Wisconsin Sequence Analysis Package, Version 8 for Unix, Genetics Computer Group, University Research Park, 575 Science Drive, Madison, Wis. 53711)).

The encoding sequence of the invention (e.g., the miRNA precursor encoding sequence or longer carrier encoding sequence) can be present in the construct in operable linkage with a promoter. Appropriate promoters can be selected based on the host cell and effect sought. Suitable promoters include constitutive and inducible promoters, such as inducible RNA polymerase II (polII)-based promoters. The promoters can be tissue specific, such promoters being well known in the art. Examples of suitable promoters include the tetracycline inducible or repressible promoter, RNA polymerase I or III-based promoters, the pol II dependent viral promoters such as the CMV-IE promoter, and the polIII U6 and H1 promoters. The bacteriophage T7 promoter can also be used (in which case, it will be appreciated, the T7 polymerase must also be present).

The constructs of the invention can be introduced into host cells using any of a variety of approaches. Infection with a viral vector comprising the construct can be effected. Examples of suitable viral vectors include replication defective retroviral vectors, adenoviral vectors, adeno-associated vectors and lentiviral vectors. Transfection with a plasmid comprising the construct is an alternative mode of introduction. The plasmid can be present as naked DNA or can be present in association with, for example, a liposome. The nature of the delivery vehicle can vary with the host cell.

In vivo delivery of the construct (e.g., present in a viral vector) can be carried out using any one of a variety of techniques, depending on the target tissue, Delivery can be, as appropriate, by direct injection, inhalation, intravenous injection or other physical method (including via microprojectiles to target visible and accessible regions of tissue (e.g., with naked DNA)). Administration can be by syringe needle, trocar, canula, catheter, etc., as appropriate.

The miRNAs of the invention can be used to regulate (e.g., inhibit) expression of target genes in cells and tissues in culture and in cells present in plants and in humans and non-human animals. The target sequences can be naturally occurring sequences, transgenes or can be pathogen sequences present, for example, as a result of infection. As one example, miRNAs of the invention can be used to "turn off" papilloma viruses in humans (e.g., in the uterus by using an appropriately designed adeno-associated viral vector).

Cultured cells suitable as hosts in accordance with the invention include both primary cells and cell lines. The cells can be human cells, including human stem cells. A construct of the invention encoding an miRNA can be introduced into cultured cells to inactivate a specific gene of unknown function. Silencing the gene using the method of the invention can be used as an approach to assess its function. Alternatively, a construct encoding an miRNA can be introduced into cells to be implanted into a human or non-human animal for therapeutic purposes. For example, hepatic stem cells can be obtained from a patient infected with hepatitis C and placed in culture. A construct of the invention encoding an miRNA that targets a gene of hepatitis C essential to, for example, replication or packaging can be introduced into the explanted cells under conditions so that the gene is silenced. The cells can then be reimplanted into the patient under conditions such that regeneration is effected.

miRNAs of the invention can also be introduced into a non-human animal to produce a model experimental animal, or into a human or non-human animal for therapeutic purposes. In the case of experimental animals, the miRNAs can be used for large scale analysis of gene function. As the target for the miRNA is about 22 nucleotides, the miRNAs can be used to knockout expression of individual isoforms resulting, for example, from alternative splicing. In the case of therapy, miRNAs can be designed, for example, to block viral replication. Human and non-human animals can be engineered, for example, to permanently express multiple miRNAs targeted to conserved sequences in viruses (e.g., packaging sequences or regulatory elements), thus rendering the humans/animals permanently immune to virus challenge, including HIV challenge. Similar approaches can be used in plants to render plants immune to viruses.

Appropriately designed miRNAs can also be used in humans and non-human animals to turn off oncogene expression in tumor cells, or inhibit expression of genes associated with other medical conditions, e.g., mutant forms of Huntingtin or of the prion protein as well as dominant negative protein mutants seen in some human genetic diseases. miRNAs of the invention can be used, for example, to inhibit expression of pro-inflammatory genes or apoptosis genes where therapeutically desirable. For instance, expression of BCL-2 can render tumor cells resistant to chemotherapy. Using the present approach, miRNAs can be used to inhibit expression of BCL-2 and enhance the ability of chemotherapeutic agents to cause tumor cells to undergo senescence, Similarly, T cells isolated from a tumor bearing patient can be modified ex vivo using the present approach to such that expression of the TGFƎ receptor is inhibited. Upon reintroduction into the patient, the killing ability of the T cells is enhanced. Likewise, T cells can be modified ex vivo to inhibit expression of the Fas receptor, thereby increasing the tumor killing capacity of the cells upon reintroduction. MiRNAs of the invention can be used to treat any disease where turning down one or a set of specific gene products is beneficial.

The miRNAs of the invention can also be used to carry out various high throughput screens to select for loss of function phenotype. For example, a library of random miRNA precursor-encoding constructs can be introduced into cells (e.g., using a viral vector) to determine function of a genomic sequence. Typically, the protocol used is such that virus is introduced per cell. Using any of a variety of approaches, those cells in which the function of the targeted gene is lost can be selected (e.g., if a gene involved in cell death resulting from viral infection is sought, only those cells that contain the targeting miRNA will remain viable after exposure to the virus; alternatively, markers (e.g., indicator proteins) can be used to select for cells containing the targeting miRNA). The miRNA can then be cloned out of the selected cells, the sequence determined and used for identifying the targeted gene.

The present invention includes compositions and kits comprising the above-described miRNAs and/or nucleic acid sequences encoding same (and constructs comprising such nucleic acids). Such compositions can further include, for example, a carrier (e.g., a sterile carrier) and such kits can further comprise, for example, ancillary reagents (e.g., buffers) such as those necessary to carry out the instant methods, and container means'.

Certain aspects of the invention are described in greater detail in the non-limiting Examples that follow (see also Zeng et al, Mol. Cell 9:1327-1333 (2002), Coburn et al, J. Virol. 76:9225-9231 (2002) and Zeng et al, RNA 9:112-123 (2003), as well as U.S. Pat. No. 6,506,559, e.g., for specific applications).

EXAMPLE 1

Experimental Procedures

Plasmid Construction and Oligonucleotide Description

The expression plasmids pBC12/CMV, pBC12/CMV/β-gal and pcRev, and the indicator constructs pDM128/RRE and pgTat, have been previously described (Malim et al, Nature 338:254-257 (1989); Bogerd et al, Crml. J. Virol. 72:8627-8635 (1998); Hope et al, Proc. Natl. Acad. Sci. USA 87:7787-7791 (1990); Cullen, Cell 46:973-982 (1986)). A GPP expression plasmid, phrGFP-6, was obtained from Strategene. To make pCMV-miR-30, the two DNA primers:

(SEQ ID NO: 1)
5'-TACTCGAGATCTGCGACTGTAAACATCCTCGACTGGAAGCTGTGAA
GCCACAGATGG-3'
and (SEQ ID NO: 2)
5'-CGCTCGAGGATCCGCAGCTGCAAACATCCGACTGAAAGCCCATCTG
TGGCTTCACAG-3' were annealed, extended using Taq DNA polymerase, cut with XhoI, and cloned into the XhoI site present in the pBC12/CMV. To make pCMV-miR-30, 5'-ATC-CCTTTCAGTCGGATGTTTGCAGCT-3' (SEQ ID NO:3) and 5'-CTAGAGCTGCAAACATCCGACTGAAAGG-3' (SEQ ID NO:4) were annealed and cloned into pBC12/CMV. To make pDMI28/RRE/4XT, four copies of the miR-30 target site (FIG. 2A, separated by two or five nucleotides from each other) were cloned into the XhoI site of pDM128/RRE. To make pgTAT-nxt, the Drosophila nxt~ coding sequence (nucleotides 1-420) were amplified from a Drosophila embryonic cDNA library and cloned between the two BglII sites present in pgTAT. The pCMV-miR-30-PTB, pCMV-miR-30-nxt and pCMV-miR-30-TAg expression plasmids were prepared as described for pCMV-miR-30, except that the inserted stem sequences were derived from each target gene.

Cell Culture and Transfection 293T cells were grown as previously described (Bogerd et al, Crml. J. Virol. 72:8627-8635 (1998)) and were transfected using FuGene 6 Reagent (Roche). CAT assays were performed at 48 hrs. after transfection, as described (Bogerd et al, Crml. J. Virol. 72:8627-8635 (1998)). For Western blotting, lysates were fractionated on a 4-20% SDS-acrylamide gradient gel (Bio-Rad), transferred, and then probed with a rabbit polyclonal antiserum directed against Tat, Rev (Malim et al, Nature 338:254-257 (1989)), CA 150 (Suné et al, Mol. Cell. Biol. 17:6029-6039 (1997)) or PTB. Reactive bands were visualized using ECL (Amersham). A polyclonal antiserum specific for human PTB 1 was prepared by immunization of rabbits with a purified recombinant fusion protein consisting of glutathione-S-transferase fused to full length PTB1. Immunofluorescence analyses were performed as described (Wiegand et al, Mol. Cell. Biol. 22:245-256 (2002)) using a monoclonal antibody against SV40 Tag (Pab 108, Santa Cruz) and rhodamine-conjugated goat anti-mouse antiserum (ICN) as well as the DNA strain DAPI.

RNA Analysis

Total RNA was isolated using Trizol Reagent (Invitrogen). Cell fractionation and RPA were performed as previously described (Kang and Cullen, Genes Dev. 13:1126-1139 (1999)). For miRNA Northern analysis, approximately 20 µg of total RNA was separated on a denaturing 15% polyacrylamide gel, transferred to a HyBond-N membrane (Amersham), UV crosslinked, and probed with 5' $^{32}$P-phosphorylated oligos in ExpressHyb solution (Clontech). For Northern analysis of mRNA, 20 µg of total RNA was fractionated on a 1% denaturing agarose gel, transferred to membrane, fixed, and probed with a random primed PTB cDNA probe.

Results

Expression of an Introduced miR-30 miRNA Sequence in Human Cells

MiR-30 is one of several novel miRNAs recently isolated from the human cell line HeLa (Lagos-Quintana et al, Science 294:853-858 (2001)). A cDNA sequence encoding the entire predicted 71 nt miR-30 precursor (FIG. 1A) was cloned into the context of an irrelevant mRNA expressed under the control of the cytomegalovirus immediate early (CMV-IE) promoter, in pCMV-miR-30. A similar plasmid, pCMV-miR-30, containing only the mature miR-30 cDNA sequence was also constructed. Human 293T cells were then transfected with these expression plasmids and total RNA was analyzed for the presence of the miR-30 miRNA by Northern blotting (FIG. 1B). Mature miR-30 could be readily detected in cells transfected with pCMV-miR-30 (FIG. 1B). The miRNA produced from the transfected pCMV-miR-30 plasmid appeared to be ~22 nt in length and had the same 5' end as reported for endogenous miR-30 (Lagos-Quintana et al, Science 294:853-858 (2001)), as determined by primer extension analysis (FIG. 1A). In contrast, mock-transfected or pCMV-miR-30 transfected 293T cells expressed no detectable miR-30 miRNA (FIG. 1B, lanes 1 and 3). Production of the miR-30 miRNA could also be detected in transfected HeLa or NIH3T3 cells or when the miR-30 precursor DNA was placed within an intron or in the 3'-UTR of another mRNA expressed under the control of the CMV-IE promoter. Thus, the mature miR-30 miRNA can be excised from the miR-30 precursor sequence when the latter is expressed within the context of an irrelevant mRNA.

Mature miR-30 is encoded by the 3' arm of its precursor (FIG. 1A), and one miRNA precursor generally gives rise to only one stable, mature miRNA species, derived from either the 5' or 3' arm of the precursor RNA hairpin (Lagos-Quintana et al, Science 294:853-858 (2001); Lau et al, Science 294: 858-862 (2001); Lee and Ambros, Science 294:862-864 (2001)). Nevertheless, it was possible to also detect a miRNA derived from the 5' arm (antisense miR-30, or anti-miR-30) in transfected cells (FIG. 1B. lane 5). While significant levels of endogenous miR-30 miRNA were not detected in either 293T cells or, surprisingly, HeLa cells, there appeared to be a low, constitutive level of endogenous anti-miR-30, or possibly of a similar miRNA, in 293T, HeLa and NIH3T3 cells (marked by "*" in FIG. 1B). MiR-30 inhibits the expression of an mRNA containing complementary target sites The *C. elegans* miRNAs lin-4 and let-7 inhibit the translation of mRNAs containing multiple complementary sequences in their 3' UTRs without significantly affecting the steady-state level of the miRNA (Lee et al, Cell 75:843-854 (1993); Wightman et al, Cell 75:855-862 (1993)). It was therefore questioned whether human miR-30 could also act via a similar mechanism. A miR-30 target sequence was designed, and four copies of this sequence were inserted into the 3' UTR of the indicator construct pDM128/RRE to give the pDM128/RRE/4XT plasmid (FIG. 2A). Importantly, this target sequence is not a perfect complement to miR-30 and instead, like known lin-4 and let-7 targets (Lee et al, Cell 75:843-854 (1993); Slack et al Mol. Cell 5:659-669 (2000)), contains a central mismatch (FIG. 2A).

The parental pDM128/RRE indicator construct used in these experiments contains 5' and 3' splice sites flanking an intron, derived from human immunodeficiency virus type 1 (HIV-1), that contains both the cat gene and the Rev Response Element (RRE) (Hope et al, Proc. Natl. Acad. Sci. USA 87:7787-7791 (1990)). As previously shown (Hope et al, Proc. Natl. Acad. Sci. USA 87:7787-7791 (1990); Bogerd et al, Crml. J. Virol. 72:8627-8635 (1998); Kang and Cullen, Genes Dev. 13:1126-1139 (1999)); nuclear export and of this unspliced cat mRNA is dependent on co-expression of the HIV-1 Rev protein, while nuclear export of the spliced mRNA encoded by pDM128/RRE, which does not encode CAT, occurs constitutively (FIG. 2). As shown in FIG. 2B, co-transfection of pCMV-miR-30, encoding the entire miR-30 RNA precursor, resulted in a marked drop in the level of CAT activity expressed from the pDM128/RRE/4XT plasmid, which contains four copies of the target site, but failed to affect CAT expression from the parental pDM128/RRE indicator plasmid (FIG. 2B). In contrast, co-transfection of pCMV-miR-30, containing only the mature miR-30 sequence, did not reduce CAT expression (FIG. 2B).

Figure 2C:
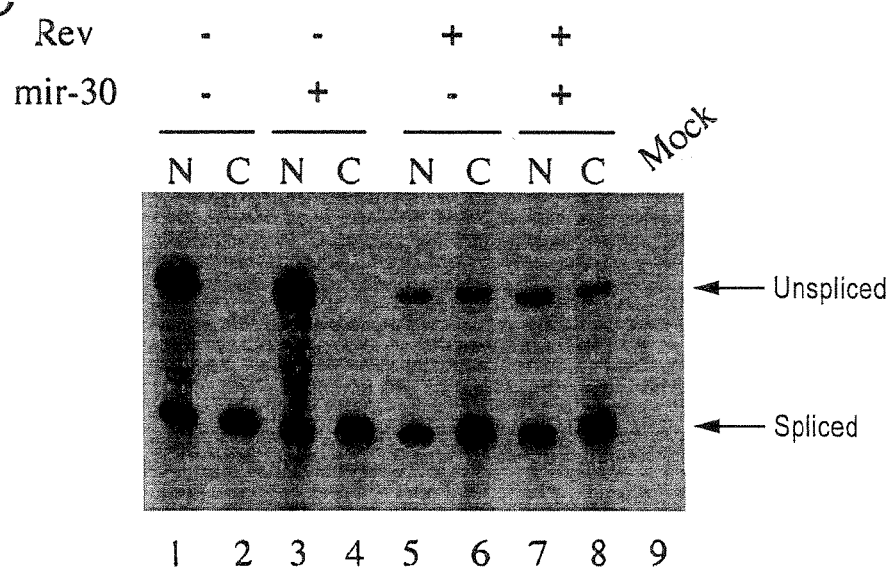

To determine whether the observed reduction in CAT activity was due to a reduction in cat mRNA expression, an RNase protection assay (RPA) was performed using nuclear and cytoplasmic RNA fractions derived from the transfected 293T cells. As shown in FIG. 2C, miR-30 did not significantly affect the cytoplasmic steady-state level of the unspliced cat mRNA encoded by pDM128/RRE/4XT (compare lanes 6 and 8). Thus, the action of the miR-30 miRNA in this reporter system appears to mimic the effect of the lin-4 miRNAs in *C. elegans* (Olsen and Ambros, Dev. Biol. 216:671-680 (1999)).

Designed miRNAs can be Produced In Vivo from Artificial miRNA Precursors

To determine whether the features found in the miR-30 precursor could be used to design and synthesize novel miRNAs in human cells, the stem sequence in the miR-30 precursor was substituted with a sequence based on the *Drosophila* nxt gene (Gene CG10174, nucleotides 121-143 from the translation initiation codon) (FIG. 3A). It has been previously shown that analogous synthetic siRNAs can block nxt mRNA expression in *Drosophila* S2 cells (Wiegand et al, Mol. Cell. Biol. 22:245-256 (2002)). Importantly, this sequence is not conserved in human nxt homologs.

The new miRNA precursor, termed miR-30-nxt, was again expressed as part of a longer mRNA transcript, as described above for wild-type miR-30. Initially, the pCMV-miR-30-nxt plasmid was transfected into human 293T cells, total RNA isolated, and the production of both the mature miR-30-nxt miRNA (the 3' arm, in accordance with miR-30) and anti-mir-30-nxt (the predicted 5' arm) analyzed by Northern analysis. In FIG. 3B (lanes 2 and 4), it is shown that both miR-30-nxt and anti-miR-30-nxt were indeed expressed. Using primer extension analysis, it was possible to determine that the 5' cleavage sites used in the synthesis of these novel miRNAs were close to those observed in the mir-30 precursor. Thus, novel miRNAs can be produced in human cells using the existing, natural miR-30 miRNA precursor as a template.

Inhibition of mRNA Expression by Designed miRNAs

To determine if endogenously transcribed miRNAs could be used as siRNAs to initiate RNAi against specific mRNA targets in mammalian cells, an indicator construct, termed pgTat-nxt, was constructed that contained an inserted 402 nucleotide sequence, derived from the *Drosophila* nxt gene, that should provide a single, fully complementary target site for the novel, miR-30-nxt miRNA. The previously described, pgTat indicator construct (Malim et al, Nature 338:254-257 (1989)) contains the two exons encoding the HLV-1 Tat protein flanking an intron, derived from the HIV-1 env gene, that also contains the HIV-1 RRE. In the absence of Rev, pgTat produces exclusively the 86 amino acid (aa), two exon form of Tat encoded by the spliced tat mRNA (FIG. 3C, lane 2). However, in the presence of the Rev nuclear RNA export factor, the unspliced mRNA encoded by pgTat is also exported from the nucleus, resulting in expression of the short, 72 aa form of the Tat protein (FIG. 3C, lane 3) (Malim et al, Nature 338:254-257 (1989)). Insertion of the nxt sequence into the intron of pgTat did not perturb this expression pattern (FIG. 3C, lanes 5 and 6). Because the target for pCMV-miR-30-nxt is only present in the intron, expression of miR-30-nxt should only affect the production of 72 aa Tat (in the presence of Rev), but not 86 aa Tat, thus providing an ideal of control for specificity. This selective inhibition was indeed observed (FIG. 3C, compare lanes 6 and 7). Importantly, miR-30-nxt did not inhibit the synthesis of the Rev protein, of the long form of Tat produced by both pgTAT and pgTAT-nxt or of the short, 72 aa form of Tat expressed from the pgTAT negative control plasmid (FIG. 3C, lanes 4 and 7).

RNAi induces the degradation of target mRNAs (Hammond et al, Nature 404:293-295 (2000); Zamore et al, Cell 101:25-33 (2000)). An RPA was therefore performed to compare the levels of spliced and unspliced Tat mRNAs in the absence or presence of Rev and miR-30-nxt. MiR-30-nxt induced a specific decrease (–7 fold) in the cytoplasmic unspliced tat mRNA level seen in the presence of Rev (compare lanes 7 and 9 in FIG. 3D), yet it had no effect on spliced tat mRNA. Similar results were obtained using a synthetic siRNA, thus strongly suggesting that the miR-30-nxt miRNA induces RNAi.

Inhibition of Endogenous Gene Expression Using Artificial miRNAs

Figure 4A:
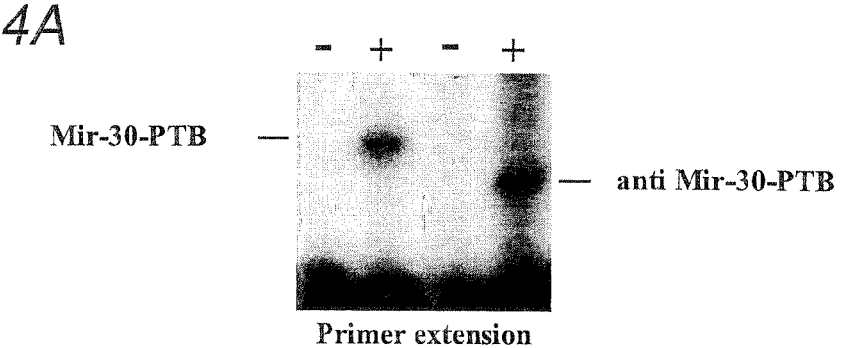
FIGS. 4A-4D. Inhibition of endogenous gene expression by novel miRNAs in 293T cells.
Figure 4B:
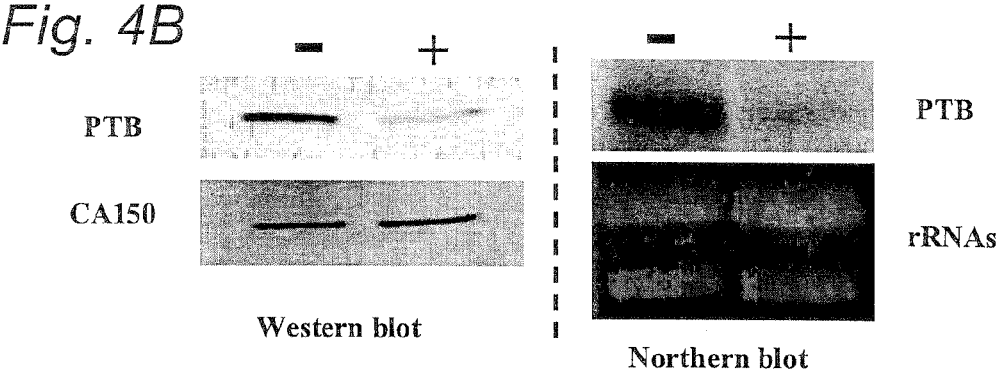

To test whether a novel miRNAs could inhibit the expression of endogenous genes in human cells, the polypyrimidine tract-binding protein (PTB) (Wagner and Garcia-Blanco, Mol. Cell. Biol. 21:3281-3288 (2001)) was chosen as a target. The pCMV-miR-30-PTB expression plasmid (containing PTB nucleoticles 1179-1201), was constructed in the same way as described for pCMV-miR-30-nxt and transfected into 293T cells. Both the miR-30-PTB and the anti-miR-30-PTB miRNA were readily detected by primer extension (FIG. 4A). Importantly, introduction of pCMV-mirR30-PTB resulted in a marked and specific reduction in the level of expression of the endogenous PTB protein and PTB mRNA, when compared to control cells (FIG. 4B).

Figure 4C:
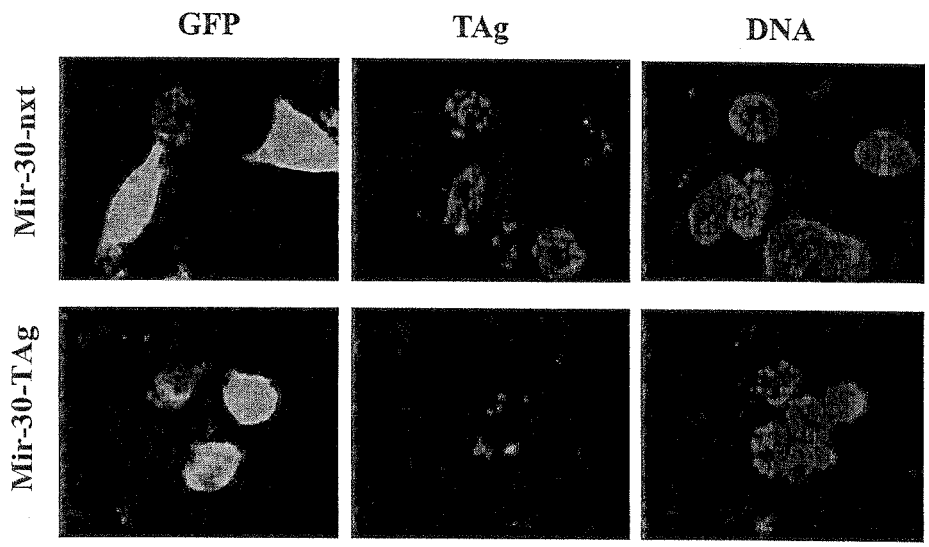
Figure 4D:
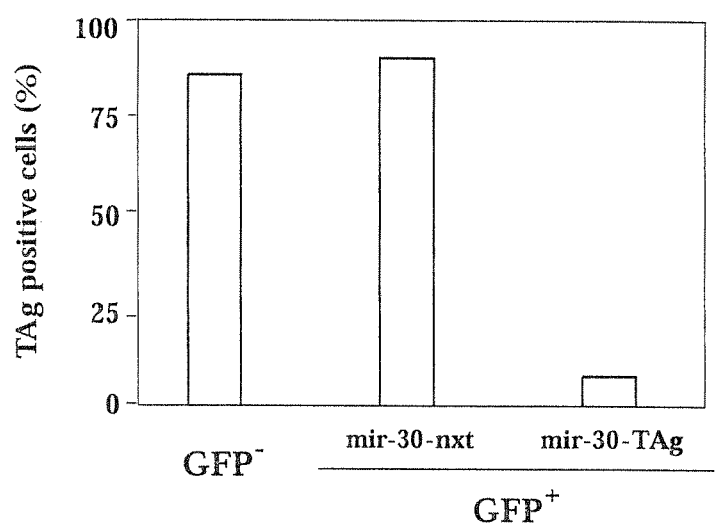

Although introduction of pCMV-miR-30-PTB resulted in a reproducible 70-80% drop in the level of PTB protein and mRNA expression in transfected 293T cells (FIG. 4B), inhibition was not complete. One possible explanation for the residual level of PTB expression is that transfection of 293T cells is not 100% efficient. To address this question, a third miRNA expression plasmid, pCMV-miR-30-Tag, was constructed that was designed to express an artificial miRNA targeted against the SV40 T antigen (Tag) (nt 639-661, Harborth et al, J. Cell Sci. 114:4557-4565 (2001)). This expression plasmid was then introduced into 293T cells, which express Tag constitutively, together with a plasmid expressing green fluorescent protein (GFP) and the number of Tag expressing cells quantitated using immunofluorescence. Co-transfection of the GFP expression plasmid made it possible to readily discriminate transfected from non-transfected cells (FIG. 4C). As shown in FIG. 4D, ~90% of cells that were not transfected, or that were transfected with GFP plus pCMV-miR-30-nxt (as a negative control) expressed readily detectable levels of TAg. In contrast, co-transfection of the pCMV-miR-30-TAg expression plasmid resulted in a dramatic reduction in the number of cells that were both GFP and TAg positive (FIGS. 4C and 4D).

It was subsequently demonstrated that a second human miRNA, termed miR-21, could also be effectively expressed when the precursor therefor formed part of a longer mRNA (Zeng et al. RNA 9:112-123 (2003)). For both miR-30 and miR-21, mature miRNA production was highly dependent on the integrity of the precursor RNA stem, although the underlying sequence had little effect.

EXAMPLE 2

Experimental Procedures

Plasmids and siRNAs.

Plasmids pCMV-miR-30, pCMV-miR-21 and pBC12/CMV/β-gal have been described (Zeng et al, RNA 9:112-123 (2003)). Indicator plasmids pCMV-luc-Target (Target being miR30(B), miR-30(AB), miR-30(P), miR-30(AP), miR-21 (B), miR-21(P), dNxt(B), dNxt(P) or random, FIG. 5A) were made by combining oligos encoding two copies of the Target sequence and inserting them after the luciferase (luc) stop codon in pCMV-luc (Zeng et al, RNA 9:112-123 (2003)). At least a 2 bp separation was introduced between adjacent target sequences. All plasmids were sequenced to verify the inserted targets. A PCR-amplified chloramphenicol acetyl transferase (CAT) expression cassette (FIG. 5B) was then cloned into the unique StuI site present in each pCMV-luc-Target intermediate. The synthetic dNxt and dTap siRNAs were obtained from Dharmacon, annealed and stored as 20:M stocks.

Transfections and Reporter Assays.

Transfections were performed in triplicate in 24-well plates. FuGene 6 (Roche) was used to transfect plasmids into 293T cells. Each well received 10 ng of pCMV-luc-Target-CAT, 8 ng of pBC12/CMV/β-gal and 400 ng of pCMV-miR-30 and/or pCMV-miR-21. For transfections involving both plasmids and siRNAs, Cellfectamine 2000 (Invitrogen) was used. Each well received 15 ng of pCMVluc-Target, 8 ng of pBC12/CMV/β-gal, 0.2 ng of pRL-CMV (Promega) and 40 pmol of the dNxt and/or dTap siRNA. 36-44 hours later, one well of cells was lysed and assayed for firefly luciferase and either CAT or Renilla luciferase (Zeng et al, RNA 9:112-123 (2003)). RNAs were isolated from the remaining two wells using Trizol Reagent (Invitrogen) or RNAeasy kits (Qiagen). Northern blotting was performed for at least two independent transfections, as previously described (Zeng et al, RNA 9:112-123 (2003)). The membranes were first hybridized with a luc probe, stripped, and then probed for β-galactosidase (β-gal) mRNA.

Results

Previously, it was demonstrated that an indicator gene can be translationally repressed in human cells upon overexpression of the human miR-30 miRNA, if the cognate mRNA bears four tandem copies of a bulged RNA target sequence in the 3'UTR (Zeng et al, Mol. Cell 9:1327-1333 (2002)). The similar indicator constructs used here are based on the firefly luciferase indicator gene and contain eight RNA target sites tandemly arrayed in the 3'UTR (FIG. 5B). This number is comparable to the seven target sites for the lin-4 miRNA found in the lin-14 mRNA 3'UTR in C. elegans (Lee et al, Cell 75:843-854 (1993), Wightman et al, Cell 75:855-862 (1993)) and was chosen in the hope of maximizing the phenotype of low levels of endogenously expressed miRNAs. The introduced target sites were either perfectly (P) homologous to the miRNAs or siRNAs used, or contained a predicted 3 nucleotide central bulge (B) (FIG. 5A). An internal control is critical for the experiments described and initial experiments therefore involved co-transfection of indicator constructs equivalent to pCMV-luc-Target (FIG. 5B) with a control plasmid encoding Renilla luciferase. In light of recent data suggesting that miRNAs can modulate the chromatin composition of genes bearing homologous DNA sequences (Dernburg et al, Cell 111:159-162 (2002)), also constructed was a second set of analogous indicator constructs, termed pCMV-luc-Target-CAT, in which the cat gene was expressed from a cassette present on the same plasmid (FIG. 5B). Closely similar data were obtained using either set of indicator plasmids.

Overexpressed Human miRNAs can Induce mRNA Cleavage.

Figure 6A:
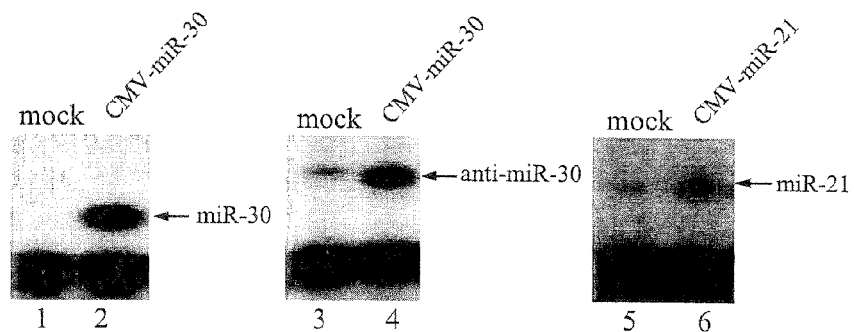
FIGS. 6A-6C. Biological activity of the miR-30 and anti-miR-30 miRNAs.

Although most miRNAs are expressed as single-stranded RNAs derived from one arm of the pre-miRNA stem-loop structure, a small number of pre-miRNAs give rise to detectable levels of a miRNA derived from both arms (Lau et al, Science 294:858-862 (2001), Mourelatos et al Genes Dev. 16:720-728 (2002)). One such miRNA is human miR-30, and its antisense form anti-miR-30, both of which have been detected in human cells (Lagos-Quintana et al, Science 294: 853-858 (2001), Mourelatos et al Genes Dev. 16:720-728 (2002)). Previously, it was reported that human 293T cells do not express detectable miR-30, but do express low levels of anti-miR-30 (FIG. 6A, lanes 1 and 3) (Zeng et al, Mol. Cell 9:1327-1333 (2002)). Transfection of 293T cells with pCMV-miR-30, which encodes the miR-30 pre-miRNA stem-loop structure contained within a longer transcript (Zeng et al, Mol. Cell 9:1327-1333 (2002)), results in overexpression of anti-miR-30 and in the production of readily detectable levels of miR-30 (FIG. 6A, lanes 2 and 4).

To assess the biological activity of these miRNAs, 293T cells were transfected with indicator constructs analogous to pCMV-luc-Target-CAT (FIG. 5B) containing eight copies of a target sequence perfectly homologous to either miR-30 [miR-30(P)] or anti-miR-30 [miR-30(AP)] or similar targets predicted to form a central 3 nucleotide RNA bulge [miR-30 (B) and miR-30(AB)]. A random 22 nt sequence served as a specificity control (FIG. 5A). Each indicator construct was co-transfected with previously described (Zeng et al, RNA 9:112-123 (2003), Zeng et al, Mol. Cell 9:1327-1333 (2002)) expression plasmids encoding either miR-30 (and anti-miR-30) or human miR21, which here serves as a negative control. In addition, these cells were also co-transfected with a plasmid encoding β-gal.

Figure 6B:
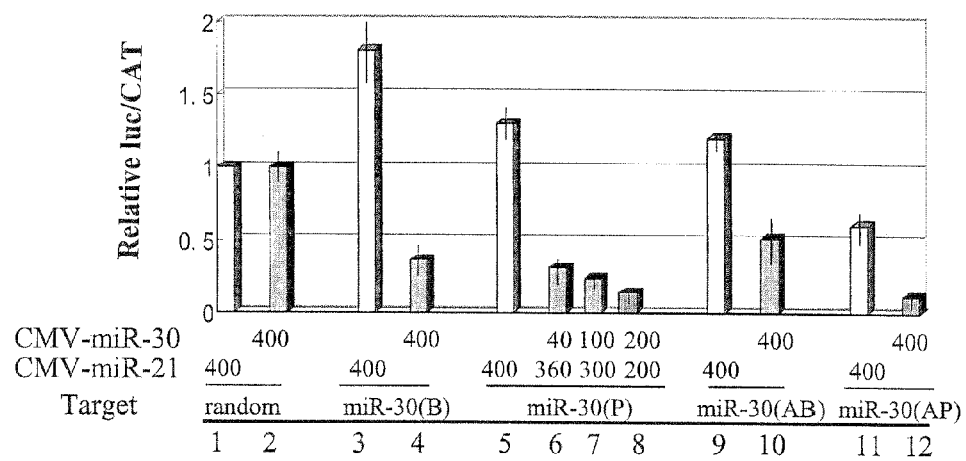

As shown in FIG. 6B, co-transfection of pCMV-miR-30 suppressed luc expression from all four indicator constructs bearing either sense or antisense miR-30 RNA targets, when compared to the pCMV-miR-21 control plasmid, but did not affect the control indicator construct bearing the random target. The two indicator plasmids encoding fully homologous, perfect (P) RNA targets were inhibited significantly more effectively than the two constructs encoding partially mismatched, bulged (B) RNA target sites when a similar level of the pCMV-miR-30 effector plasmid was co-transfected. However, equivalent levels of inhibition of luc expression were achievable by, for example, co-transfecting an ~10 fold lower level of pCMV-miR-30 with the pCMV-luc-miR-30 (P)-CAT indicator construct (FIG. 6B).

The control indicator construct, bearing eight tandem copies of a random target sequence, consistently gave rise to an ~1.8 fold lower level of luciferase activity than was seen with the indicator construct bearing the miR-30 (B) target site in the absence of overexpressed miR-30 miRNA. While not wishing to be bound by theory, it is hypothesized that this lower activity may reflect a weak, non-specific cis effect of the random sequence used. Despite the possibility that insertion of sequences into the 3' UTR of an mRNA could exert a non-specific effect on mRNA function, it is nevertheless of interest, given that 293T cells express a low level of endogenous anti-miR-30, but not miR-30, miRNA (FIG. 6A), that both indicator constructs predicted to be responsive to anti-miR30 gave rise to significantly lower levels of luciferase than did the matched indicator plasmids specific for miR-30 (FIG. 6B, compare columns 3 and 5 with 9 and 11). This observation is consistent with the hypothesis that these indicator constructs are subject to partial inhibition by the endogenous anti-miR-30 miRNA.

Figure 6C:
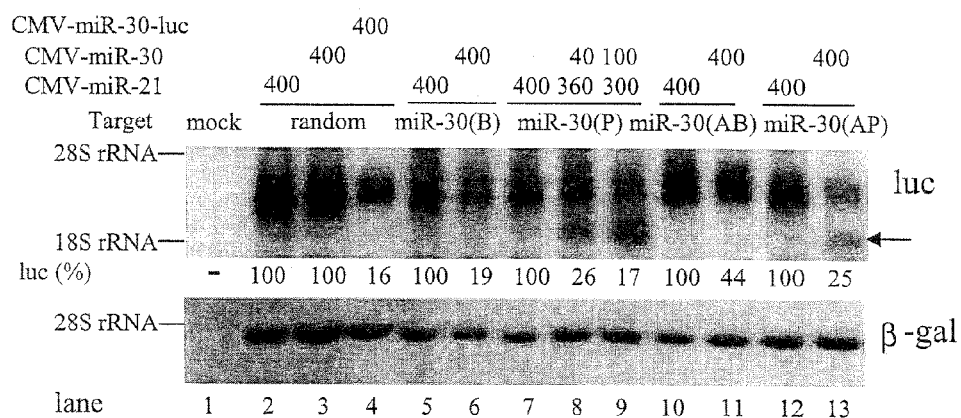

To gain insight into the mechanism of inhibition of luciferase expression documented in FIG. 6B, a northern analysis was next performed that measured the level of expression of both the luc mRNA and the β-gal internal control mRNA (FIG. 6C). Consistent with the protein data, luc mRNA levels encoded by the indicator construct bearing random target sites were unaffected by miR-30 or miR-21 expression, although they were sharply reduced by co-transfection of a previously described plasmid (Zeng et al, RNA 9:112-123 (2003)), termed pCMV-miR30-luc, that encodes an siRNA that is specific for the luc open reading frame (FIG. 6C, lanes 2-4). An important observation emerged upon comparison of the luc mRNA expression pattern in cultures transfected with indicator plasmids bearing perfect versus bulged RNA targets. Specifically, while all cultures gave rise to detectable levels of the full-length, ~2.3 kb luc mRNA, the cultures transfected with pCMV-miR-30 and indicator plasmids bearing perfect targets were distinct in also giving rise to a second luc mRNA band of ~1.8 kb in size (FIG. 6C, lanes 8, 9 and 13). This is the predicted size of the 5' fragment of the full-length luc miRNA that would arise upon cleavage within the 3'UTR target sites (FIG. 5B) and therefore suggests that both miR-30 (FIG. 6C, lanes 8 and 9) and anti-miR-30 (FIG. 6C, lane 13) are able to induce the specific cleavage of an mRNA bearing perfect target sites when overexpressed. Importantly, the lack of detectable cleavage of closely similar luc mRNAs bearing bulged target sites (FIG. 6C, lanes 6 and 11) is not due simply to a lower level of inhibition, as the shorter luc mRNA band remained readily detectable when RNA was prepared from cells co-transfected with the indicator construct bearing the perfect target sites together with a low level of pCMV-miR-30 designed to mimic the level of inhibition seen when the target sites were bulged (compare lanes 6 and 8, FIG. 6C).

Cleavage of an mRNA by an Endogenous Human miRNA.

Unlike miR-30, but like the majority of miRNAs, processing of the miR-21 pre-miRNA gives rise to only one stable mature miRNA (Lagos-Quintana, Science 294:853-858 (2001), Zeng et al, RNA 9:112-123 (2003)). Although miR-21 is expressed at readily detectable levels in 293T cells, this miRNA (but not its putative antisense partner) can be overexpressed by transfection of 293T cells with the pCMV-miR-21 expression plasmid (FIG. 6A, lanes 5 and 6).

Figure 7A:
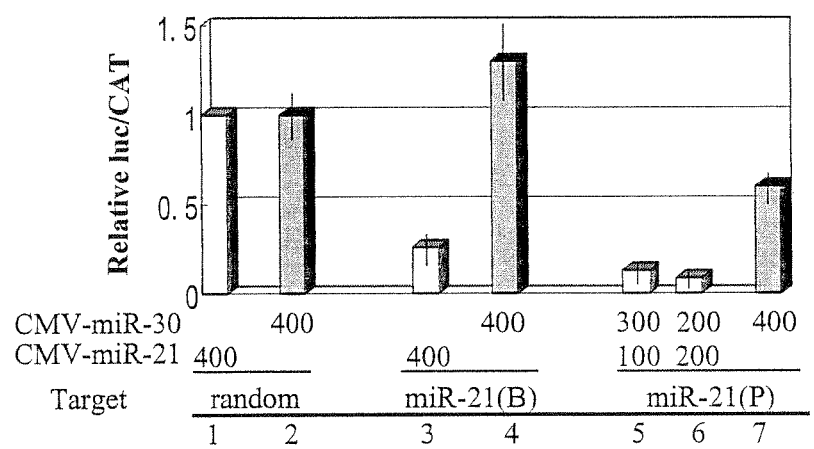
FIGS. 7A and 7B. Biological activity of the human miR-21 miRNA.

Indicator constructs analogous to pCMV-luc-Target-CAT, but containing eight copies of a perfect or bulged target specific for miR-21 (FIG. 5A), were constructed and their biological activity analyzed. As shown in FIG. 7A, these constructs behaved similarly to the equivalent constructs analyzed in FIG. 6A, in that both the bulged and perfect target sites supported specific inhibition by the co-transfected pCMV-miR-21 effector plasmid, with the perfect indicator again being somewhat more responsive. Of note, the pCMV-luc-miR-21(P)-CAT indicator construct gave rise to a quite low level of luc enzyme expression even in the absence of a co-transfected effector plasmid, thus again suggesting inhibition by endogenous miR-21 (FIG. 7A, lane 7).

Analysis of mRNA expression by northern blot analysis revealed readily detectable levels of the ~1.8 kb luc mRNA cleavage product in cultures transfected with the indicator construct bearing the miR-21(P) target but not the miR-21(B) target (FIG. 7B, lanes 2, 4 and 5), as previously also seen with miR-30 (FIG. 6C). Importantly, however, this cleavage product was also readily detectable, albeit at a lower level, in pCMV-luc-miR-21(P)-CAT transfected cultures that were not co-transfected with pCMV-miR-21 (FIG. 6B, lane 6). The simplest explanation for this observation is that the endogenous miR-21 miRNA is responsible for cleavage of the miR-21(P) luc indicator mRNA within the fully homologous target sequence. In contrast, neither endogenous nor overexpressed miR-21 is able to induce mRNA cleavage when this target bears a central mismatch (FIG. 6C, lanes 2 and 3). Similarly, the low level of endogenous anti-miR-30 miRNA (FIG. 6A) also gave rise to a low level of cleavage of the mRNA encoded by the pCMV-luc-miR-30(AP)-CAT indicator construct in some experiments, although the resultant mRNA cleavage product was present at levels only barely above background (FIG. 6C, lane 12).

Inhibition of mRNA Translation by a Synthetic siRNA.

Having established that both overexpressed and endogenous miRNAs can cleave target mRNAs, the next question was whether synthetic siRNAs can inhibit mRNA function without inducing mRNA cleavage. To address this issue, two synthetic siRNAs specific for mRNAs encoding the *Drosophila* Nxt and Tap proteins were utilized. While these reagents can inhibit dNxt and dTap protein and mRNA expression in transfected *Drosophila* S2 cells (Wiegand et al, Mol. Cell. Biol. 22:245-256 (2002)), these target nucleotide sequences are not conserved in the human Nxt and Tap genes.

Figure 8A:
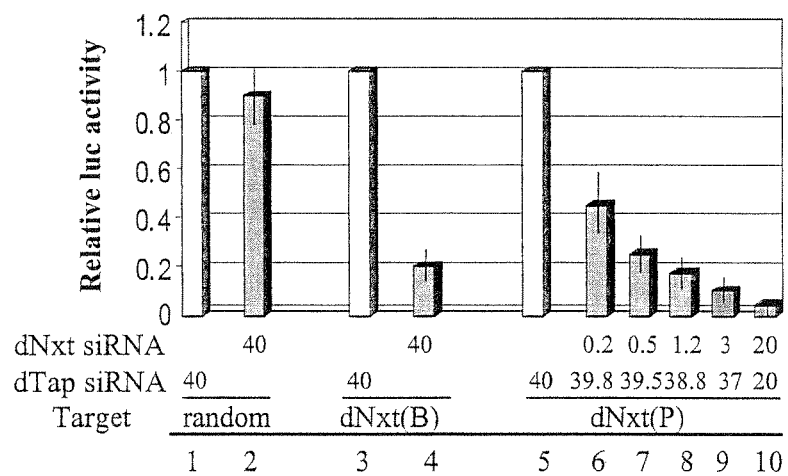
FIGS. 8A and 8B. Inhibition of mRNA utilization by a synthetic siRNA.
Figure 8B:
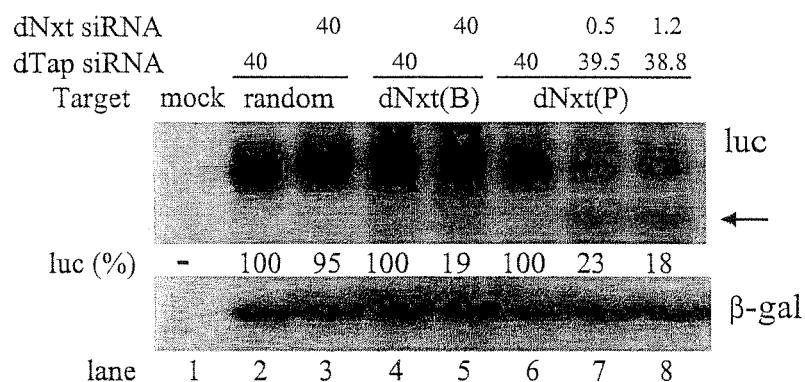

Indicator constructs based on pCMV-luc-Target, bearing perfect or bulged target sequences homologous to the dNxt siRNA (FIG. 5A) were transfected into 293T cells along with either the dNxt or dTap siRNA (the latter as a negative control) and a β-gal expression plasmid. As shown in FIG. 8A, both the bulged and perfect dNxt target supported specific inhibition of luc protein expression upon dNxt siRNA co-transfection, although the perfect target was again more responsive than the bulged target. Analysis of luc mRNA expression by northern blot revealed a drop in the level of full-length luc mRNA and the appearance of the predicted truncated luc mRNA fragment in cultures transfected with the construct bearing the perfect dNxt target, even when inhibition of luc enzyme activity was only a relatively modest ~5 fold (FIG. 8B, lanes 7 and 8). In contrast, an equivalent ~5 fold inhibition of the construct bearing the bulged dNxt target failed to give rise to any detectable truncated luc mRNA and indeed failed to significantly affect the level of expression the full length luc mRNA (FIG. 8B, lane 5). It was, therefore, concluded that the inhibition of luc enzyme expression seen with the indicator construct bearing the bulged dNxt targets is due not to cleavage and degradation of the target luc mRNA but rather to some form of translational inhibition.

In summary, using entirely in vivo assays in human cells, it has been demonstrated that endogenous human miR-21 miRNA, or overexpressed forms of the human miR-30 and anti-miR-30 miRNAs, can induce the cleavage of mRNAs bearing fully complementary target sites, a phenotype previously viewed as characteristic of siRNAs (FIGS. 5 and 7). Conversely, it has also been demonstrated that a synthetic siRNA is able to downregulate the expression of an mRNA bearing partially mismatched, bulged target sites, without inducing detectable mRNA cleavage or reducing mRNA expression levels (FIG. 8), an attribute previously viewed as characteristic of miRNAs (Hutv<gner et al, Curr. Opin. Genet. Dev. 12:225-232 (2002))). Together, these data indicate that miRNAs and siRNAs interact identically with mRNA molecules bearing target sites of equivalent complementarity, i.e., in both cases perfect homology leads to mRNA cleavage while a central bulge induces translational inhibition. These observations confirm and extend recent in vitro data documenting the specific cleavage of an artificial RNA target by a cytoplasmic extract containing the human miRNA let-7 (Hutv<gner et al, Science 297:2056-2060 (2002)).

Figure 7B:
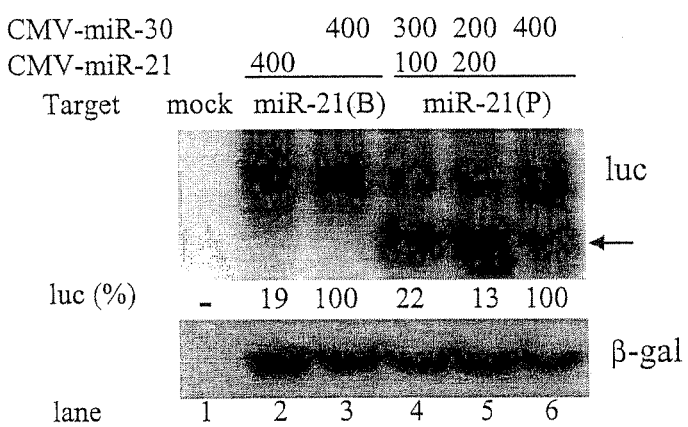

Interpretation of the foregoing data was greatly facilitated by the finding that the ~2.3 kb luc mRNA encoded by the indicator constructs used gives rise to a stable ~1.8 kb 5' breakdown product after siRNA- or miRNA-mediated cleavage at the introduced target sites. This RNA intermediate was invariably detected when a miRNA or siRNA encountered a fully complementary artificial target but was never seen when the target was designed with a central mismatch (FIG. 6C, FIG. 7B and FIG. 8B). This RNA also differed from full-length luc mRNA in that only the latter was detectable by Northern analysis when a probe specific for sequences 3' to the introduced target sites was tested. While the stability of this mRNA fragment is clearly fortuitous, others have previously detected the appearance of a stable luc mRNA cleavage intermediate in cells treated with a luc-specific siRNA (Gitlin et al, Nature 418:320-434 (2002)).

Although the data presented above demonstrate that miRNAs and siRNAs can inhibit mRNA expression by apparently identical mechanisms, it could be argued that siRNAs might still be more effective at RNA degradation than at translation inhibition, while miRNAs might display the converse activity. However, both for miRNAs and siRNAs, significantly more effective inhibition of luc enzyme activity was observed if the luc mRNA bore a fully complementary target and was therefore subject to RNA cleavage (FIGS. 6B, 7A and 8A). This could, of course, simply reflect more efficient recruitment of miRNA- or siRNA-containing ribonucleoprotein complexes to higher affinity RNA binding sites. However, while RISC appears to function as a true RNA cleavage enzyme when presented with fully complementary RNA target sites (Hutvágner et al, Science 297:2056-2060 (2002)), it is speculated that target site mismatches that preclude cleavage, such as a central RNA bulge, may freeze RISC in place on the mismatched RNA target. In this manner, centrally mismatched RNA targets may reduce the effective concentration of their cognate RISC complex and thereby reduce the efficiency with which mRNA expression is inhibited.

All documents cited above are hereby incorporated in their entirety by reference.

What is claimed is:

1. A composition comprising a carrier and a DNA construct comprising a constitutive or inducible promoter operably linked to a nucleic acid comprising a sequence encoding an artificial micro RNA (miRNA) precursor, wherein said artificial miRNA precursor is a naturally occurring miRNA precursor a portion of the stem of the stem loop structure of said naturally occurring miRNA precursor being substituted by an exogenous sequence complementary to a portion of an RNA transcript of a target gene in a cell, wherein, following introduction of said construct into said cell:
i) said nucleic acid is transcribed so that a transcript comprising said artificial miRNA precursor is produced,
ii) said transcript resulting from step (i) is processed so that said artificial miRNA precursor is excised therefrom,
iii) said artificial miRNA precursor resulting from step (ii) is processed so that a mature miRNA about 21 or 22 nucleotides in length is excised from said artificial miRNA precursor, and
iv) inhibition of expression of said gene is effected.

2. A kit comprising a container, said container comprising the composition according to claim 1.

3. An isolated human or non-human animal cell comprising a DNA construct comprising a constitutive or inducible promoter operably linked to a nucleic acid comprising a sequence encoding an artificial micro RNA (miRNA) precursor, wherein said artificial miRNA precursor is a naturally occurring miRNA precursor a portion of the stem of the stem loop structure of said naturally occurring miRNA precursor being substituted by an exogenous sequence complementary to a portion of an RNA transcript of a target gene in said cell, wherein, following introduction of said construct into said cell:
i) said nucleic acid is transcribed so that a transcript comprising said artificial miRNA precursor is produced,
ii) said transcript resulting from step (i) is processed so that said artificial miRNA precursor is excised therefrom,
iii) said artificial miRNA precursor resulting from step (ii) is processed so that a mature miRNA about 21 or 22 nucleotides in length is excised from said artificial miRNA precursor, and
iv) inhibition of expression of said gene is effected.

4. The composition of claim 1 wherein said naturally occurring miRNA precursor is a naturally occurring human or non-human animal miRNA precursor.

5. The cell of claim 3 wherein said naturally occurring miRNA precursor is a naturally occurring human or non-human animal miRNA precursor.

6. The composition of claim 4 wherein said naturally occurring human or non-human animal miRNA precursor is a mir-30 precursor.

7. The cell of claim 5 wherein said naturally occurring human or non-human animal miRNA precursor is a mir-30 precursor.

8. The composition of claim 4 wherein said naturally occurring human or non-human animal miRNA precursor is a mir-21 precursor.

9. The cell of claim 5 wherein said naturally occurring human or non-human animal miRNA precursor is a mir-21 precursor.

10. The composition of claim 1 wherein said naturally occurring miRNA precursor is a naturally occurring plant miRNA precursor.

11. The composition of claim 1 wherein said promoter is a polymerase II-based promoter.

12. The cell of claim 3 wherein said promoter is a polymerase II-based promoter.

13. The composition of claim 1 wherein said promoter is a tissue specific promoter.

14. The cell of claim 3 wherein said promoter is a tissue specific promoter.

15. The composition of claim 1 wherein said promoter is an inducible promoter.

16. The cell of claim 3 wherein said promoter is an inducible promoter.

17. The composition of claim 1 wherein said nucleic acid comprises a sequence encoding more than one artificial miRNA precursor.

18. The cell of claim 3 wherein said nucleic acid comprises a sequence encoding more than one artificial miRNA precursor.

19. The composition of claim 1 wherein said stem of said stem loop structure of said artificial miRNA precursor includes at least one bulge.

20. The cell of claim 3 wherein said stem of said stem loop structure of said artificial miRNA precursor includes at least one bulge.

21. The composition of claim 1 wherein said construct is present in a viral vector or a plasmid.

22. The cell of claim 3 wherein said construct is present in a viral vector or a plasmid.

23. The composition of claim 1 wherein said construct is present in a lentiviral vector.

24. The cell of claim 3 wherein said construct is present in a lentiviral vector.

25. The composition of claim 1 wherein said gene is a cellular gene, a transgene or a pathogen gene.

26. The cell of claim 3 wherein said gene is a cellular gene, a transgene or a pathogen gene.

27. The composition of claim 1 wherein said transcript of said nucleic acid comprises nucleotide sequences that flank said stem loop structure of said artificial mlRNA precursor.

28. The cell of claim 3 wherein said transcript of said nucleic acid comprises nucleotide sequences that flank said stem loop structure of said artificial mlRNA precursor.

29. A composition comprising a carrier and a DNA construct comprising a constitutive or inducible promoter operably linked to a nucleic acid comprising a sequence encoding a naturally occurring microRNA (miRNA) precursor, wherein a portion of the stem of the stem loop structure of said miRNA precursor is complementary to a portion of an RNA transcript of said gene, wherein, following introduction of said construct into a cell:

i) said nucleic acid is transcribed so that a transcript comprising said miRNA precursor is produced, ii) said transcript resulting from step (i) is processed so that said miRNA precursor is excised therefrom, iii) said miRNA precursor resulting from step (ii) is processed so that a mature miRNA about 21 or 22 nucleotides in length is excised from said miRNA precursor, and iv) inhibition of expression of said gene is effected.

30. A kit comprising a container, said container comprising the composition according to claim 29.

31. An isolated human or non-human animal cell comprising a DNA construct comprising a constitutive or inducible promoter operably linked to a nucleic acid comprising a sequence encoding a naturally occurring microRNA (miRNA) precursor, wherein a portion of the stem of the stem loop structure of said miRNA precursor is complementary to a portion of an RNA transcript of said gene, wherein, following introduction of said construct into a cell:

i) said nucleic acid is transcribed so that a transcript comprising said miRNA precursor is produced, ii) said transcript resulting from step (i) is processed so that said miRNA precursor is excised therefrom, iii) said miRNA precursor resulting from step (ii) is processed so that a mature miRNA about 21or 22 nucleotides in length is excised from said miRNA precursor, and iv) inhibition of expression of said gene is effected.

\* \* \* \* \*

SEQUENCE LISTING

<160> NUMBER OF SEQ ID NOS: 25

<210> SEQ ID NO 1

-continued

```
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 1
tactcgagat ctgcgactgt aaacatcctc gactggaagc tgtgaagcca cagatgg       57

<210> SEQ ID NO 2
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 2
cgctcgagga tccgcagctg caaacatccg actgaaagcc catctgtggc ttcacag       57

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
atccctttca gtcggatgtt tgcagct                                        27

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 4
ctagagctgc aaacatccga ctgaaagg                                       28

<210> SEQ ID NO 5
<211> LENGTH: 71
<212> TYPE: RNA
<213> ORGANISM: Artificial Sequence
<220> FEATURE:
<223> OTHER INFORMATION: Description of Artificial Sequence: Predicted
      human mir-30 precursor RNA

<400> SEQUENCE: 5
gcgacuguaa acauccucga cuggaagcug ugaagccaca gaugggcuuu cagucggaug    60
uuugcagcug c                                                         71

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence:
      Synthetically designed target site

<400> SEQUENCE: 6
gcugcaaaca aagacugaaa g                                              21

<210> SEQ ID NO 7
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      mir-30 target site

<400> SEQUENCE: 7
cuuucagucg gauguuugca gc                                              22

<210> SEQ ID NO 8
<211> LENGTH: 67
<212> TYPE: RNA
<213> ORGANISM: Artificial Sequence
<220> FEATURE:
<223> OTHER INFORMATION: Description of Artificial Sequence: Synthetic
      mir-30-nxt precursor sequence

<400> SEQUENCE: 8
gcgcaugcua cgcuuagcug gaauggguga agccacagau gccauuccag cuaagcguag     60
cauuugc                                                               67

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 9
cuuucagucg gauguuugca gc                                              22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 10
gcugcaaaca agggacugaa ag                                              22

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 11
cuuucagucg gauguuugca gc                                              22

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 12
gcugcaaaca uccgacugaa ag                                              22

<210> SEQ ID NO 13
<211> LENGTH: 24
<212> TYPE: RNA
```

```
<213> ORGANISM: Artificial Sequence
<220> FEATURE:
<223> OTHER INFORMATION: Description of Artificial Sequence: Synthetic
      RNA target sequence

<400> SEQUENCE: 13
uguaaacauc cucgacugga agcu                                              24

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 14
gcuuccaguc cucgauguuu ac                                                22

<210> SEQ ID NO 15
<211> LENGTH: 24
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 15
uguaaacauc cucgacugga agcu                                              24

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 16
gcuuccaguc gaggauguuu ac                                                22

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 17
uagcuuauca gacugauguu ga                                                22

<210> SEQ ID NO 18
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 18
ucaacaucag agagauaagc ua                                                22

<210> SEQ ID NO 19
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      RNA target sequence

<400> SEQUENCE: 19
uagcuuauca gacugauguu ga                                                22

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 20
ucaacaucag ucugauaagc ua                                                22

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 21
auuccagcua agcguagcau u                                                 21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 22
aaugcuacgg aaagcuggaa u                                                 21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 23
auuccagcua agcguagcau u                                                 21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      RNA target sequence

<400> SEQUENCE: 24
aaugcuacgc uuagcuggaa u                                                 21

<210> SEQ ID NO 25
<211> LENGTH: 22
<212> TYPE: RNA
<213> ORGANISM: Artificial Sequence
<220> FEATURE:
```

```
<223> OTHER INFORMATION: Description of Artificial Sequence: Synthetic
      RNA target sequence

<400> SEQUENCE: 25
cgguacaaac cugccaguaa ga                                                22
```